Figure 1:
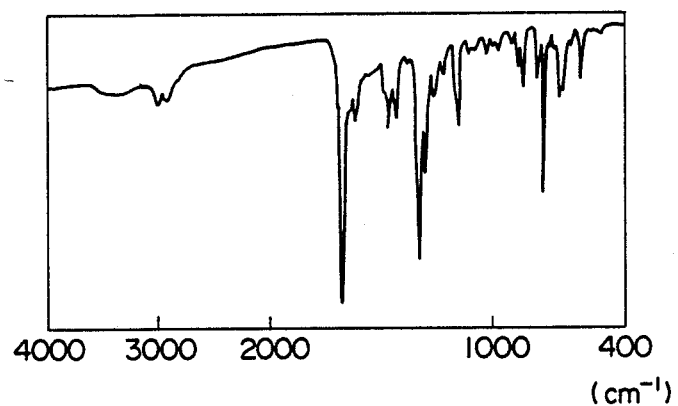

United States Patent [19]

Kato et al.

[11] Patent Number: 4,895,587

[45] Date of Patent: Jan. 23, 1990

[54] HALOACETAMIDE COMPOUNDS, PROCESS FOR PRODUCTION THEREOF, AND USE THEREOF AS HERBICIDE

[75] Inventors: Shozo Kato, Fujisawa; Tetsuo Takematsu, Utsunomiya; Hidenori Okamoto, Fujisawa; Masaru Ogasawara, Utsunomiya, all of Japan

[73] Assignee: Tokuyama Soda Kabushiki Kaisha, Yamaguchi, Japan

[21] Appl. No.: 875,686

[22] Filed: Jun. 18, 1986

[30] Foreign Application Priority Data

Jun. 21, 1985 [JP] Japan .................................. 60-134387

[51] Int. Cl.⁴ ...................... A01N 37/18; A01N 43/02; C07C 103/34; C07C 103/37
[52] U.S. Cl. .......................................... 71/90; 71/92; 71/118; 564/209; 564/210; 564/212; 549/77
[58] Field of Search ...................... 564/209, 210, 212; 71/90, 92, 118; 549/77

[56] References Cited

U.S. PATENT DOCUMENTS

| | | | |
|---|---|---|---|
| 2,706,727 | 4/1955 | Chupp et al. | 564/209 X |
| 3,287,106 | 11/1966 | Chupp | 564/209 X |
| 3,608,087 | 9/1971 | Hoff et al. | 564/209 X |
| 4,033,756 | 7/1977 | Hoffmann | 564/209 X |
| 4,195,036 | 3/1980 | Gozzo et al. | 564/209 |
| 4,228,101 | 10/1980 | Gozzo et al. | 564/209 |
| 4,258,196 | 3/1981 | Chupp et al. | 564/209 X |
| 4,330,323 | 5/1982 | Gorny et al. | 564/209 X |
| 4,391,626 | 7/1983 | Stetter | 564/209 X |
| 4,443,628 | 4/1984 | Rinehart | 564/209 |
| 4,531,970 | 7/1985 | Rinehart | 564/209 X |
| 4,600,433 | 7/1986 | Alt | 71/118 |

Primary Examiner—Paul F. Shaver
Attorney, Agent, or Firm—Sherman and Shalloway

[57] ABSTRACT

A haloacetamide compound of the following formula (I)

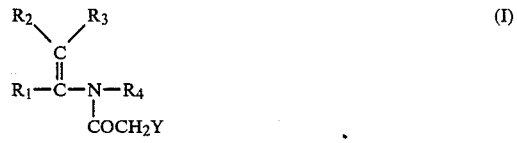

wherein
$R_1$ represents a substituted or unsubstituted $C_6$–$C_{14}$ aryl group or a substituted or unsubstituted $C_3$–$C_8$ heteroaryl group having one or two hetero atoms selected from the group consisting of O, S and N,
$R_2$ and $R_3$, independently from each other, represent a hydrogen atom, a $C_1$–$C_6$ alkyl group or a $C_1$–$C_6$ alkoxy group, or $R_2$ and $R_3$, taken together, represent a $C_2$–$C_{16}$ alkylene group,
$R_4$ represents a substituted or unsubstituted $C_1$–$C_{12}$ alkyl group, a substituted or unsubstituted $C_6$–$C_{14}$ aryl group, a $C_2$–$C_{12}$ alkenyl grup or a $C_2$–$C_{12}$ alkynyl group, and
Y represents a halogen atom selected from the group consisting of Cl, Br and I;
and its use as herbicide.

5 Claims, 1 Drawing Sheet

HALOACETAMIDE COMPOUNDS, PROCESS FOR PRODUCTION THEREOF, AND USE THEREOF AS HERBICIDE

This invention relates to haloacetamide compounds not described in the prior known literature, a process for production thereof, and to their use as a herbicide.

More specifically, this invention relates to a haloacetamide compound of the following formula (I)

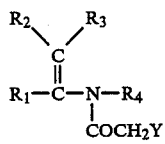

wherein
- $R_1$ represents a substituted or unsubstituted $C_6$-$C_{14}$ aryl group or a substituted or unsubstituted $C_3$-$C_8$ heteroaryl group having one or two hetero atoms selected from the group consisting of O, S and N,
- $R_2$ and $R_3$, independently from each other, represent a hydrogen atom, a $C_1$-$C_6$ alkyl group or a $C_1$-$C_6$ alkoxy group, or $R_2$ and $R_3$, taken together, represent a $C_2$-$C_{16}$ alkylene group,
- $R_2$ represents a substituted or unsubstituted $C_1$-$C_{12}$ alkyl group, a substituted or unsubstituted $C_6$-$C_{14}$ aryl group, a $C_2$-$C_{12}$ alkenyl group or a $C_2$-$C_{12}$ alkynyl group, and
- Y represents a halogen atom selected from the group consisting of Cl, Br and I.

This invention also pertains a process for producing the compound of formula (I), a herbicidal composition comprising the compound of formula (I) as an active ingredient, and to a method of controlling the growth of undesired vegetation using the compound of forfmula (I).

It has been known that N-(l-alkenyl)-chloroacetanilides of the following formula (A) re useful as a herbicide or a plant growth regulator (Japanese Laid-Open Patent Publication No. 947/1983 laid-open on Jan. 6, 1983 corresponding to West German Patent Application P 3120990.4).

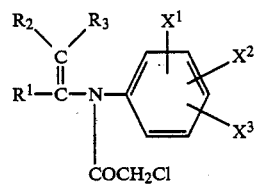

In the formula:
- $R^1$ represents a hydrogen atom or an alkyl group,
- $R^2$ represents a hydrogen atom, or an alkyl, alkoxy, alkoxyalkyl, hydroxyalkyl or benzyl group,
- $R^3$ represents a hydrogen atom, or an alkyl, alkenyl, alkoxy, alkoxyalkyl, alkylcarbonyl, alkylcarboxylalkyl, alkoxycarbonyl or alkoxycarbonylalkyl group, provided that $R^1$ and $R^2$, taken together with a double bond C=C, may represent an optionally substituted mono- or poly-unsaturated ring which may contain a hetero atom and/or a carbonyl group, or $R^2$ and $R^3$, taken together with the adjacent carbon atom, may represent an optionally substituted saturated or unsaturated ring which may contain a hetero atom, or $R^2$ and $R^3$ both represent a group of the formula

in which $R^6$ represents a hydrogen atom or an alkyl group and $R^7$ represents an alkyl or phenyl group, and $X^1$, $X^2$ and $X^3$, independently from each other, represents a hydrogen or halogen atom or an alkyl group.

When the known chloroacetamide compounds of formula (A) are used as a herbicide in concentrations sufficient to obtain a satisfactory herbicidal efficacy, they cause unnegligible phytotoxicity to crop plants. Their herbicidal use is therefore limited.

The present inventors have extensively worked in order to develop herbicidal compounds which have a broad herbicidal spectrum against paddy weeds and upland farm weeds, exhibit a satisfactory herbicidal efficacy when applied in relatively low concentrations, and do not cause phytotoxicity to crops and plants or toxicity to warm-blooded animals including man, domestic animals and poultry.

Their work has resulted in successful synthesis of the compounds of formula (I) which are not described in the known literature, and has led to the discovery that these compounds show herbicidal activity against paddy weeds and upland farm weeds with a broad herbicidal spectrum. Investigations of the present inventors have shown that the compounds of formula (I) show a satisfactory herbicidal effect at relatively low rates of application, and can control the growth of undesired vegetation without causing toxicity to crops and plants and warm-blooded animals.

It has also been found as a result of research work by the present inventors that for the exhibition of the improved herbicidal activity mentioned above, it is critical that $R_1$ in the basic skeleton specified in formula (I) should be a specific aryl or heteroaryl group unlike the known compounds of formula (A).

It is an object of this invention therefore to provide novel haloacetamide compounds not described in the prior known literature which are useful, for example, for controlling the growth of undesired vegetation.

Another object of this invention is to provide a process for producing these novel haloacetamide compounds, the use of these compounds as a herbicide, and a method of conrolling the growth of undesired vegetation using these compounds.

The above and other objects of this invention along with its advantages will become more apparent from the following description.

The novel haloacetamide compounds of this invention are represented by the following formula (I).

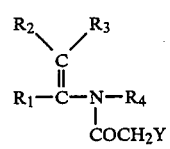

In formula (I), $R_1$ represents a substituted or unsubstituted $C_6$-$C_{14}$ aryl group or a substituted or unsubstituted $C_3$–$C_8$ heteroaryl group having one or two hetero atoms selected from the group consisting of O, S and N.

Examples of the aryl group for $R_1$ are phenyl, naphthyl, anthranyl and phenanthrenyl groups. The phenyl or naphthyl group is preferred. Examples of the heteroaryl group are furyl, thienyl, pyrrolyl, benzofuryl, benzothienyl, indolyl, thiazolyl, pyrazolyl, imidazolyl and pyridyl goups. The 5-membered heteroaryl groups and 5-membered heteroaryl groups having a fused carbon ring are preferred.

The aryl or heteroaryl group represented by $R_1$ may have a substituent. Examples of the substituent include $C_1$–$C_6$ alkyl groups, halogen atoms, $C_1$–$C_6$ alkoxy groups, $C_1$–$C_6$ haloalkyl groups, $C_1$–$C_6$ alkylthio groups, a phenoxy group, substituted phenoxy groups having a substituent selected from $C_1$–$C_6$ alkyl groups and halogen atoms (Cl, Br, I and F), a phenyl group, and substituted phenyl groups having a substituent selected from $C_1$–$C_6$ alkyl groups and halogen atoms (Cl, Br, I and F).

Examples of the substituent $C_1$–$C_6$ alkyl group mentioned above are methyl, ethyl, n- or iso-propyl, n-iso- or tert-butyl, n-pentyl, and n-hexyl groups. Examples of the substituent halogen atom above are Cl, Br, I and F. Examples of the substituent $C_1$–$C_6$ alkoxy group above are methoxy, ethoxy, n- or iso-propoxy, n-, iso- or tert-butoxy, pentyloxy and hexyloxy groups. Examples of the $C_1$–$C_6$ alkyl group which the substituted phenoxy or phenyl group may have are the same as those given for the substituent $C_1$–$C_6$ alkyl group above.

Specific examples of the aryl groups for $R_1$ substituted by such substituents include alkylphenyl groups such as methylphenyl, dimethylphenyl, ethylphenyl, diethylphenyl, propylphenyl, dipropylphenyl, butylphenyl, pentylphenyl, hexylphenyl, methylethylphenyl, methylprophylphenyl and ethylpropylphenyl groups; halophenyl groups such as fluorophenyl, difluorophenyl, chlorophenyl, dichlorophenyl, bromophenyl, iodophenyl, trichlorophenyl and chlorofluorophenyl groups; alkoxyphenyl groups such as methoxyphenyl, dimethoxyphenyl, trimethoxyphenyl, ethoxyphenyl, diethoxyphenyl, propoxyphenyl and butoxyphenyl groups; (haloalkyl)phenyl groups such as (chloromethyl)phenyl, (chloroethyl)phenyl, (chloropropyl)phenyl, (bromopropyl)phenyl, (fluoroethyl)phenyl, (difluoromethyl)phenyl, (trifluoromethyl)phenyl and (difluorobromomethyl)phenyl groups; alkylthiophenyl groups such as methylthiophenyl, ethylthiophenyl, propylthiophenyl and butylthiophenyl groups; phenoxyphenyl groups such as phenoxyphenyl, (methylphenoxy)phenyl, (ethylphenoxy)phenyl, (butylphenoxy)phenyl, (chlorophenoxy)phenyl, (bromophenoxy)phenyl, (fluorophenoxy)phenyl and (chloromethylphenoxy)phenyl groups; phenylphenyl groups such as (methylphenyl)phenyl, (ethylphenyl)phenyl, (propylphenyl)phenyl, (chlorophenyl)phenyl, (bromohenyl)phenyl, (fluorohenyl)phenyl and (iodophenyl)phenyl groups; substitutd phenyl groups such as chloro(methyl)phenyl, chloro(ethoxy)phenyl and methyl(methoxy)phenyl groups; and other substituted aryl groups such as methylnaphthyl, dimethylnaphthyl, ethylnaphthyl, chloronaphthyl, bromonaphthyl, dichloronaphthyl, methoxynaphthyl, (trifluoromethyl)naphthyl, methylthionaphthyl, phenoxynaphthyl, chlorophenoxynaphthyl, methylphenoxynaphthyl, phenylnaphthyl, chlorophenylnaphthyl, methylanthranyl, ethylanthranyl, chloroanthranyl, bromoanthranyl, methoxyanthranyl, methylthioanthranyl, phenoxyanthranyl, phenylanthrayl, methylphenanthryl, chlorophenanthryl, ethoxyphenanthryl and ethylthiophenanthryl.

Specific examples of the heteroaryl group for $R_1$ substituted by the above-illustrated substituents include substituted furyl groups such as methylfuryl, dimethylfuryl, ethylfuryl, propylfuryl, chlorofuryl, bromofuryl, methoxyfuryl, ethoxyfuryl, propoxyfuryl, (trifluoromethyl)furyl, methlthiofuryl, ethylthiofuryl, phenoxyfuryl, (chlorophenoxy)furyl, phenylfuryl and methylphenylfuryl groups; substituted thienyl groups such as methylthienyl, ethylthienyl, propylthienyl, butylthienyl, fluorothienyl, chlorothienyl, bromothienyl, iodothienyl, methoxythienyl, ethoxythienyl, propoxythienyl, (chloroethyl)thienyl, (trifluoromethyl)thienyl, methylthiothienyl, ethylthiothienyl, dibromothienyl, dimethoxythienyl, phenoxythienyl, (methylphenoxy)thienyl and chlorophenylthienyl groups; substituted pyrrolyl groups such as N-methylpyrrolyl, N-ethylpyrrolyl, methyl-N-methylpyrrolyl, chloro-N-ethylpyrrolyl, methoxy-N-methylpyrrolyl, (trifluoromethyl)-N-methylpyrrolyl, methylthio-N-ethylpyrrolyl, phenoxy-N-methylpyrrolyl and phenyl-N-ethylpyrrolyl groups; substituted benzofuryl groups such as methylbenzofuryl, chlorobenzofuryl, ethoxybenzofuryl, (trifluoromethyl)benzofuryl and phenoxybenzofuryl groups; substituted benzothienyl groups such as ethylbenzothienyl, fluorobenzothienyl, methoxybenzothienyl, methylthiobenzothienyl and phenylbenzothienyl groups; a methylthiazolyl group; substituted pyrazolyl groups such as dimethylpyrazolyl and phenylpyrazolyl groups; and substituted imidazolyl groups such as methoxyimidazolyl and phenylimidazolyl groups.

In formula (I) in this invention, $R_2$ and $R_3$, independently from each other, represent a hydrogen atom, a $C_1$–$C_6$ alkyl group or a $C_1$–$C_6$ alkoxy group, or $R_2$ and $R_3$, taken together, represent a $C_2$–$C_{16}$ alkylene group in which case $R_2$ and $R_3$ form a cycloalkylene group having 3 to 17 carbon atoms including the carbon atom to which they are bonded.

The $C_1$–$C_6$ alkyl group includes linear or branched alkyl groups having 1 to 6 carbon atoms, and specific examples are methyl, ethyl, n-propyl, iso-propyl, n-butyl, iso-butyl, n-pentyl an n-hexyl groups.

Specific examples of the $C_1$–$C_6$ alkoxy group are methoxy, ethoxy, propoxy, butoxy, pentyloxy, and hexyloxyl groups.

Examples of the alkylene group having 2 to 16 carbon atoms which may be formed by linking of $R_2$ and $R_3$ are ethylene, trimethylene, tetramethylene, pentamethylene, hexamethylene, heptamethylene, octamethylene, decamethylene and undecamethylene groups.

In the compound of formula (I) in accordance with this invention, $R_4$ represents a substituted or unsubstituted $C_1$–$C_{12}$ alkyl group, a substituted or unsubstituted $C_6$–$C_{14}$ aryl group, a $C_2$–$C_{12}$ alkenyl group or a $C_2$–$C_{12}$ alkynyl group.

The $C_1$–$C_{12}$ alkyl group includes linear or branched alkyl groups, and specific examples include, methyl, ethyl, n-propyl, iso-propyl, n-butyl, iso-butyl, pentyl, hexyl, heptyl, octyl, nonyl, decyl, undecyl and dodecyl groups.

Examples of the $C_6$–$C_{14}$ aryl group include phenyl, naphthyl, anthranyl and phenanthrenyl groups. The phenyl or naphthyl group is preferred.

Examples of the $C_2$–$C_{12}$ alkenyl group include ethenyl, propenyl, butenyl, pentenyl, hexenyl, heptenyl, octenyl, decenyl and dodecenyl groups. The $C_2$–$C_6$ alkenyl groups are preferred.

Examples of the $C_2$-$C_{12}$ alkynyl group include ethynyl, propynyl, butynyl, pentynyl, hexynyl, heptynyl, octynyl, decynyl and dodecynyl groups. The $C_2$-$C_6$ alkynyl groups are preferred.

The $C_1$-$C_{12}$ alkyl group for $R_4$ may be substituted by substituents. Examples of the substituents for the alkyl group $R_4$ include halogen atoms; $C_1$-$C_6$ alkoxy groups; $C_1$-$C_6$ alkylthio groups; a phenoxy group; substituted phenoxy groups having a substituent selected from $C_1$-$C_6$ alkyl groups, $C_1$-$C_6$ alkoxy groups, $C_1$-$C_6$ alkylthio groups and halogen atoms; a cyano group; a phenyl group; substituted phenyl groups having substituent selected from $C_1$-$C_6$ alkyl groups, $C_1$-$C_6$ alkoxy groups, $C_1$-$C_6$ alkythio groups and halogen atoms; $C_3$-$C_5$ heteroaryl groups having one or two hetero atoms selected from O, S and N which are unsubstituted or substituted by a substituent selected from $C_1$-$C_6$ alkyl groups and halogen atoms; $C_2$-$C_6$ heterocycloalkyl groups having one or two hetero atoms selected from O, S and N which are unsubstituted or substituted by $C_1$-$C_6$ alkyl groups; alkoxycarbonyl groups having 1 to 6 carbon atoms in the alkoxy moiety; alkylcarbonyloxy groups having 1 to 6 carbon atoms in the alkyl moiety, which may optionally be substituted by halogen atoms; $C_2$-$C_6$ alkenyloxy groups and $C_2$-$C_6$ alkynyl groups.

With regard to the substituents on the alkyl group $R_4$, examples of the halogen atoms are Cl, Br, I and F, and examples of the $C_1$-$C_6$ alkoxy groups are methoxy, ethoxy, n-propoxy, iso-propoxy, n-butoxy, iso-butoxy, n-pentyloxy, and n-hexyloxy groups. Examples of the $C_1$-$C_6$ alkythio groups are methylthio, ethylthio, n- or iso-propylthio, n- or iso-butylthio, pentylthio and hexylthio groups. Examples of the $C_1$-$C_6$ alkyl group for the phenoxy group are methyl, ethyl, n- or iso-propyl, n- or iso-butyl, pentyl and hexyl groups. Examples of the $C_1$-$C_6$ alkoxy and $C_1$-$C_6$ alkylthio groups and halogen atoms as the substituents for the phenoxy group may be the same as those given hereinabove. Examples of the substituents for the phenyl group may be the same as the substituents cited above as examples of the substituents for the phenoxy group. Furthermore, examples of the $C_1$-$C_6$ alkyl groups and halogen atoms as substituents for the $C_3$-$C_5$ heteroaryl group may be the same alkyl groups and halogen atoms as given above. Examples of the $C_3$-$C_5$ heteroaryl group may be those heteroaryl groups having 3 to 5 carbon atoms exemplified with regard to the heteroaryl group for $R_1$. Examples of the $C_2$-$C_6$ heterocycloalkyl group which the substituents for the alkyl group $R_4$ may have include tetrahydrofuryl, tetrahydrothienyl, pyrrolidyl, tetrahydropyryl, tetrahydrothiopyryl and piperidyl groups. Examples of the $C_1$-$C_6$ alkyl substituent which these heterocycloalkyl groups may have are the same $C_1$-$C_6$ alkyl groups given above with regard to the substituents for the phenoxy group. Examples of the alkoxycarbonyl groups having 1 to 6 carbon atoms in the alkoxy moiety are methoxycarbonyl, ethoxycarbonyl, propoxycarbonyl, butoxycarbonyl and pentoxycarbonyl groups. Examples of the alkylcarbonyloxy groups having a $C_1$-$C_6$ alkyl group optionally substituted by a halogen atom are methylcarbonyloxy, ethylcarbonyloxy, propylcarbonyloxy, butylcarbonyloxy, pentylcarbonyloxy, (chloromethyl)carbonyloxy, (bromoethyl)cabonyloxy, (fluoropropyl)carbonyloxy, (dichloropropyl)carbonyloxy and (trifluorobutyl)carbonyloxy groups. Examples of the $C_2$-$C_6$ alkenyloxy groups are ethenyloxy, propenyloxy, butenyloxy, pentenyloxy, and hexenyloxy groups. Examples of the $C_2$-$C_6$ alkynyloxy groups are ethynyloxy, propynyloxy, butynyloxy, pentynyloxy and hexynyloxy groups.

In the compounds of formula (I) in accordance with this invention, the $C_6$-$C_{14}$ aryl group for $R_4$ may have a substituent. Examples of the substituents are halogen atoms, $C_1$-$C_6$ alkyl groups which are unsubstituted or substituted by halogen atoms, $C_1$-$C_6$ alkylthio groups and $C_1$-$C_6$ alkoxy groups. Examples of the halogen atoms are Cl, Br, I and F. Examples of the $C_1$-$C_6$ alkyl groups are methyl, ethyl, n- or iso-propyl, n- or iso-butyl, pentyl and hexyl groups. Examples of the halogen atoms which the alkyl group may have are Cl, Br, I and F.

Specific examples of the substituted $C_1$-$C_{12}$ alkyl group for $R_4$ include linear or branched haloalkyl groups such as fluoromethyl, trifluoromethyl, chloromethyl, trichloromethyl, chloroethyl, bromoethyl, fluoropropyl, chloropropyl, chlorobutyl, bromopentyl and chlorohexyl groups; linear or branched alkoxyalkyl groups such as methoxymethyl, methoxyethyl, dimethoxyethyl, methoxypropyl, methoxybutyl, methoxypentyl, methoxyhexyl, ethoxymethyl, ethoxyethyl, diethoxyethyl, ethoxypropyl, diethoxypropyl, ethoxybutyl, propoxymethyl, propoxyethyl, propoxypropyl, propoxybutyl, butoxymethyl, butoxyethyl, butoxypropyl, butoxybutyl and pentoxyethyl groups; phenoxyalkyl groups such as phenoxymethyl, phenoxyethyl, (methylthiophenoxy)methyl, (bromophenoxy)ethyl, (chlorophenoxy)ethyl, (methylphenoxy)ethyl, (propoxyphenoxy)-ethyl and (chlorophenoxy)propyl groups; cyanoalkyl groups such as cyanoethyl, cyanopropyl and cyanobutyl groups; alkythioalkyl groups such as methylthiomethyl, methylthioethyl, methylthiopropyl, ethylthiomethyl, ethylthioethyl, ethylthiobutyl and propylthioethyl groups; phenylalkyl groups such as phenylmethyl, phenylethyl, phenylpropyl, (ethylthiophenyl)methyl and (chlorophenyl)propyl groups; heteroarylalkyl groups such as thienylmethyl, thienylethyl, methoxythienylmethyl, furylmethyl, furylethyl, chlorofurylmethyl, pyrrolylmethyl, pyrrolylethyl, pyrazolylmethyl, pyrazolylethyl and imidazolylethyl; heterocycloalkylalkyl groups such as tetrahydrofurylmethyl, tetrahydrofurylethyl, methyltetrahydrofurylethyl, pyrrolidyl ethyl, piperidylethyl, N-methylpyrrolidylethyl, N-methylpyrrolidlmethyl, methylpiperidylpropyl, tetrahydrothienylmethyl and tetrahydrothienylethyl groups; alkoxycarbonylalkyl groups such as methoxycarbonylmethyl, methoxycarbonylethyl, ethoxycarbonylmethyl, ethoxycabonylethyl, propoxycarbonylethyl, ethoxycarbonylpropyl and butoxycarbonylpropyl groups; alkylcarbonyloxyalkyl groups such as methylcarbonyloxymethyl, methylcarbonyloxyethyl, methylcarbonyloxypropyl, ethylcarbonyloxymethyl, ethylcarbonyloxyethyl, ethylcarbonyloxypropyl, propylcarbonyloxyethyl, (chloromethyl) carbonyloxymethyl, (chloromethyl)carbonyloxyethyl, (chloroethyl)carbonyloxyethyl and (fluoroethyl)carbonyloxyethyl groups; alkenyloxyalkyl groups such as ethenyloxymethyl, ethenyloxyethyl, propenyloxymethyl, propenyloxyethyl, propenyloxypropyl, propenyloxybutyl, butenyloxyethyl, and butenyloxypropyl; and alkynyloxyalkyl groups such as ethynyloxymethyl, ethynyloxyethyl, propynyloxymethyl, propynyloxyethyl, propynyloxypropyl, propynyloxybutyl and butynyloxyethyl groups.

In general formula (I), Y is a halogen atom selected from chlorine, bromine and iodine atoms. Y is preferably a chlorine or bromine atom.

Compounds of formula (I) having the groups specifically exmplified hereinabove, in many cases, include various position isomers. Such isomers may be utilized in this invention without any particular restriction. For example, the methylphenyl group includes o-methylphenyl, m-methylphenyl and p-methylphenyl, and the butyl group includes n-butyl, sec-butyl and tert-butyl.

The structure of the compound of general formula (I) in accordance with this invention can be determined by the following procedures.

(A) By measuring the infrared absorption spectrum (ir) of the compound, an absorption near 3200–2800 cm$^{-1}$ assigned to the CH bond, a strong absorption near 1680–1670 cm$^{-1}$ assigned to the carbonyl linkage of the amide group, and a weak absorption near 1640–1620 cm$^{-1}$ assigned to the C=C bond can be observed.

(B) The mass spectrum (ms) of the compound is measured, and the composition formula corresponding to the individual peaks observed (generally the mass number m/e obtained by dividing the ion molecular weight m by the ion charge number e). This gives information on the molecular weight of the compound and the manner of bonding the atomic groupings in the molecule. When the compound is represented by the following general formula

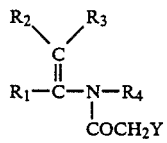

the molecular ion peaks (to be abbreviated M⊕) are generally observed by the intensity ratio in accordance with the ratio of existing isotopes according to the number of halogen atoms contained in the molecule, and therefore, the molecular weight of the compound can be determined. In the compound of general formula (I), characteristic peaks corresponding to M⊕-Y and M⊕-COCH$_2$Y are observed, and the manner of bonding of the molecules can be known.

Figure 2:
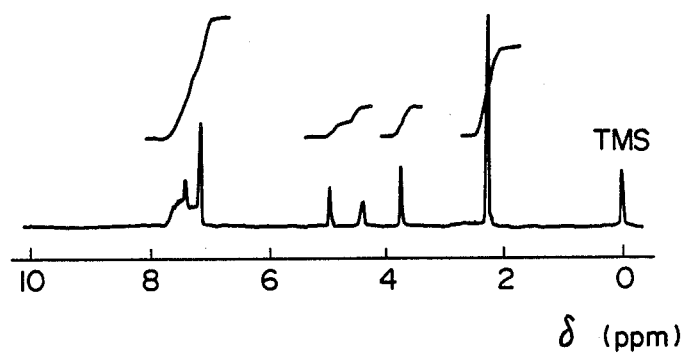

(C) By measuring the $^1$H-nuclear magnetic resonance spectrum ($^1$H-nmr), the manner of bonding of hydrogen atoms present in the compound can be determined. As a typical example of the $^1$H-nmr (δ, ppm: tetramethylsilane as an internal standard, deuterochloroform as a solvent) of the compound of general formula (I), the $^1$H-nmr chart of N-[1-(phenyl)ethenyl]-N-chloroaceto-2′,6′-dimethylanilide is shown in FIG. 2. The results of its analysis are as follows:

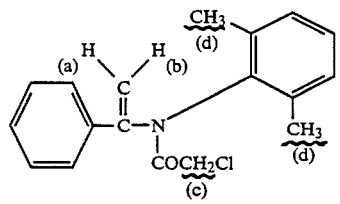

A singlet corresponding to 6 protons based on the methyl group (d) is observed at 230 ppm; a singlet corresponding to 2 protons based on the chloroacetyl group (c), at 3.75 ppm; two singlets corresponding to 1 proton based on the ethenyl groups (a) and (b), at 4.41 ppm and 4.97 ppm; and a multiplet corresponding to 8 protons based on the benzene ring, at 7.10 ppm to 7.60 ppm.

(D) The weight percents of carbon, hydrogen, nitrogen and halogen (sulfur as well when the compound contains it) are determined by elemental analysis. By subtracting the total of the recognized weight percents of the individual elements from 100, the weight percent of oxygen can be calculated. Accordingly, the composition formula of the compound can be determined.

The haloacetamide compounds of this invention differ somewhat in properties depending upon the types of R$_1$, R$_2$, R$_3$, R$_4$ and Y in general formula (I) and the degree of purification. Generally, they are pale yellow to blackish brown viscous liquids or solids at ordinary temperature and atmospheric pressure. Specific properties will be shown in Examples. The compounds of this invention are soluble in general organic solvents such as benzene, ethers, alcohols, chloroform, acetonitrile, dimethylformamide and dimethylsulfoxide, but are only sparingly soluble in water.

According to this invention, various novel haloacetamide compounds can be provided by selecting R$_1$, R$_2$, R$_3$, R$_4$ and Y in general formula (I). Specific examples of typical compounds of general formula (I) are shown below.

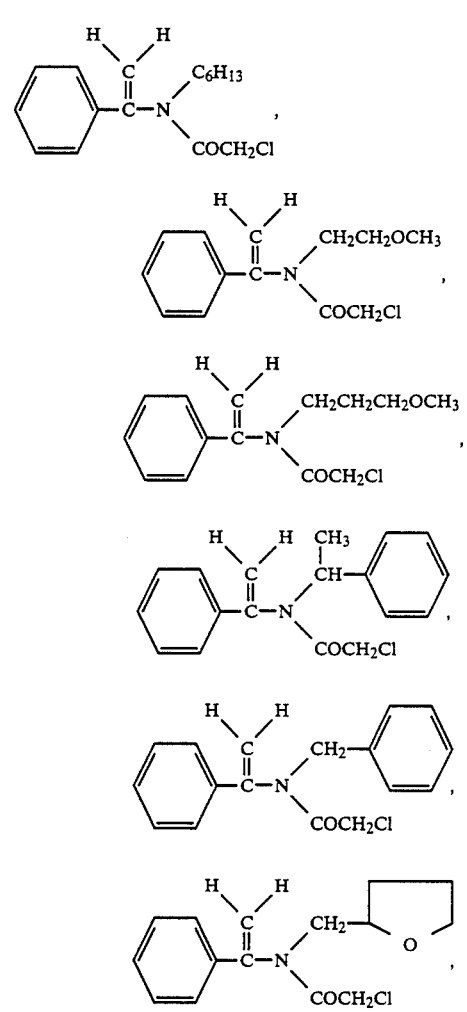

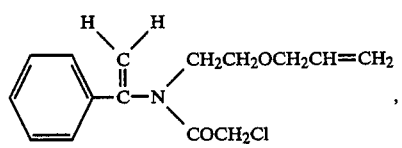
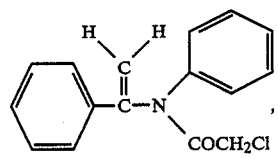
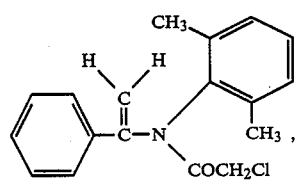
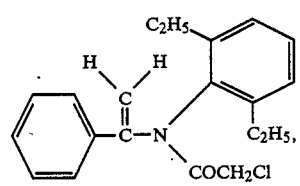
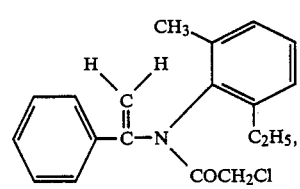
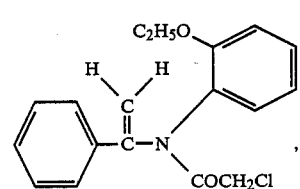
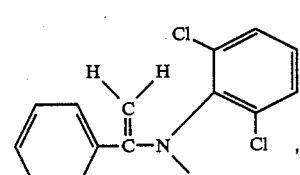
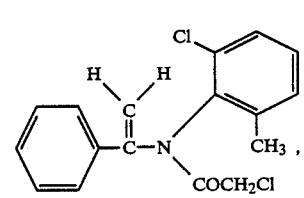
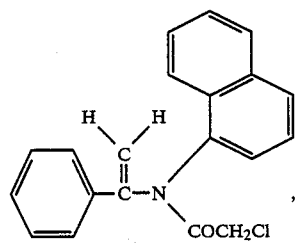
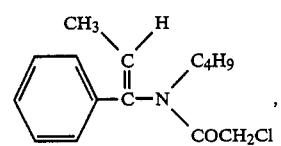
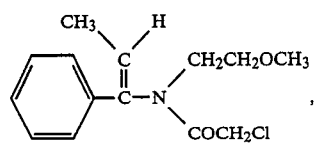
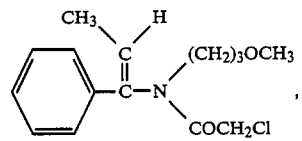
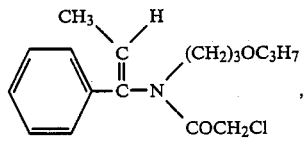
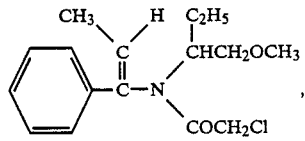
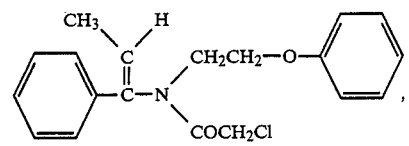
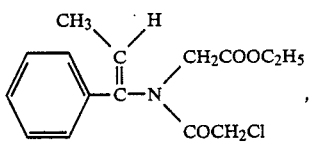
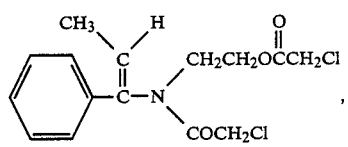
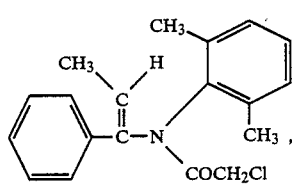

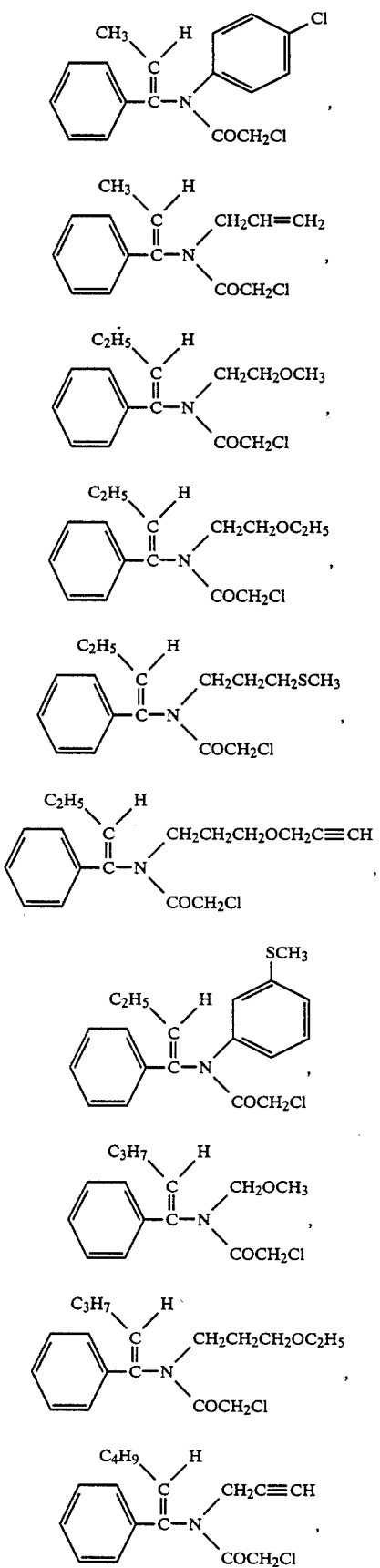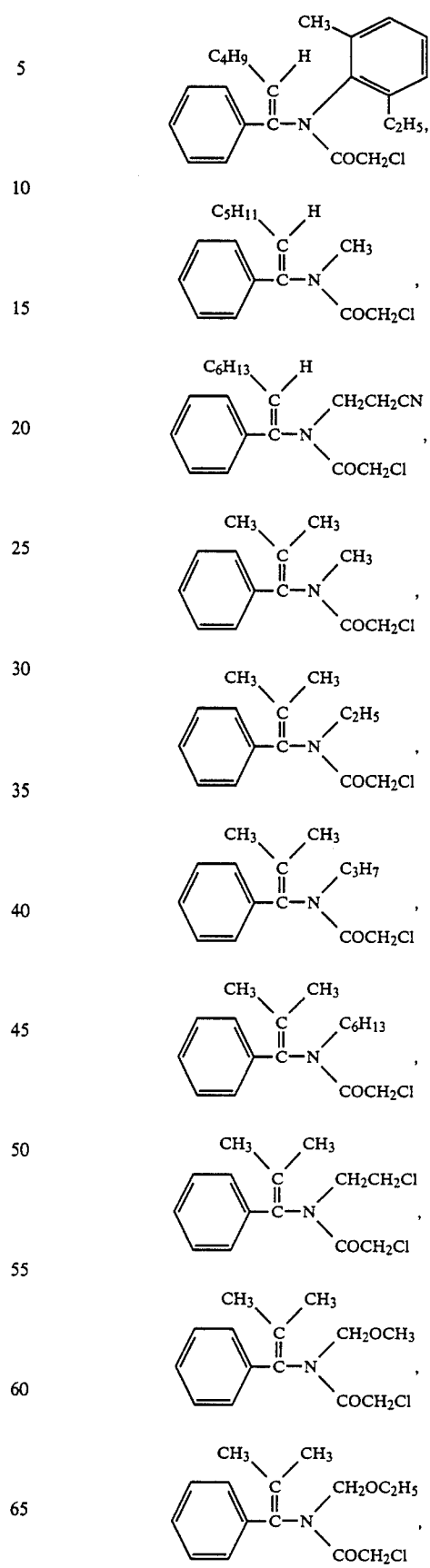

-continued (Structures continuing list of chemical compounds, all sharing a common core: a phenyl group with C=N where the carbon bears two CH3 substituents, and the nitrogen bears a COCH2Cl group plus a variable R group.)

Column 1 (page 13) R groups:
- CH2CH2OCH3
- CH2CH2OC2H5
- CH2CH2OC3H7
- CH2CH2OC5H11
- CH2CH(OCH3)2
- CH2CH(OC2H5)2
- CH2CH2CH2OCH3
- CH2CH2CH2OC2H5
- CH2CH2CH2OC3H7
- (CH2)4OCH3
- CH2CH2CH2SCH3

Column 2 (page 14) R groups:
- CH2CH2—O—(4-chlorophenyl)
- CH2—phenyl
- CH2—(2-methoxyphenyl)
- CH2CH2CN
- CH2—(furan-2-yl)
- CH2—(tetrahydrofuran-2-yl)
- CH(CH3)—(pyrazol-1-yl)
- CH2—(imidazol-1-yl)
- CH2COOC2H5
- CH(CH3)COOCH3

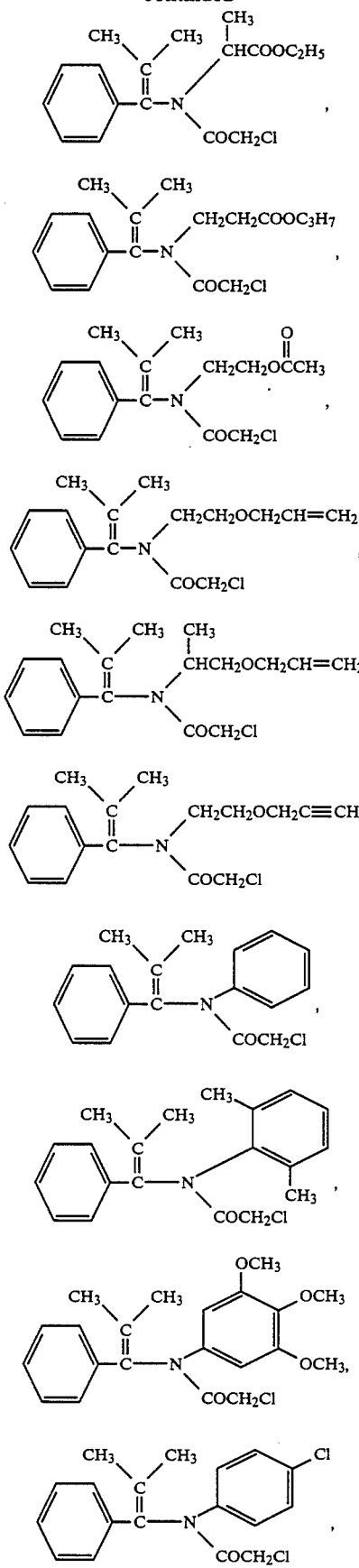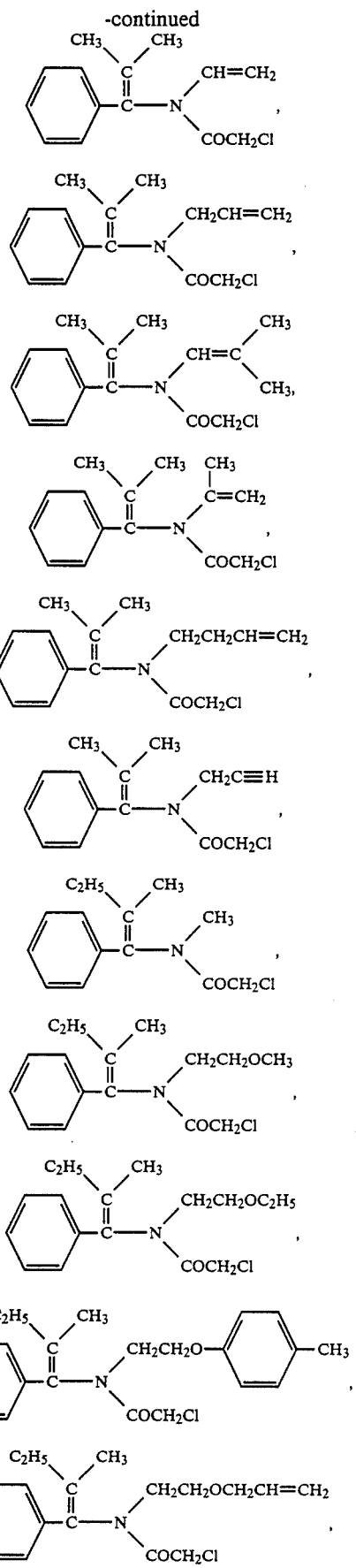

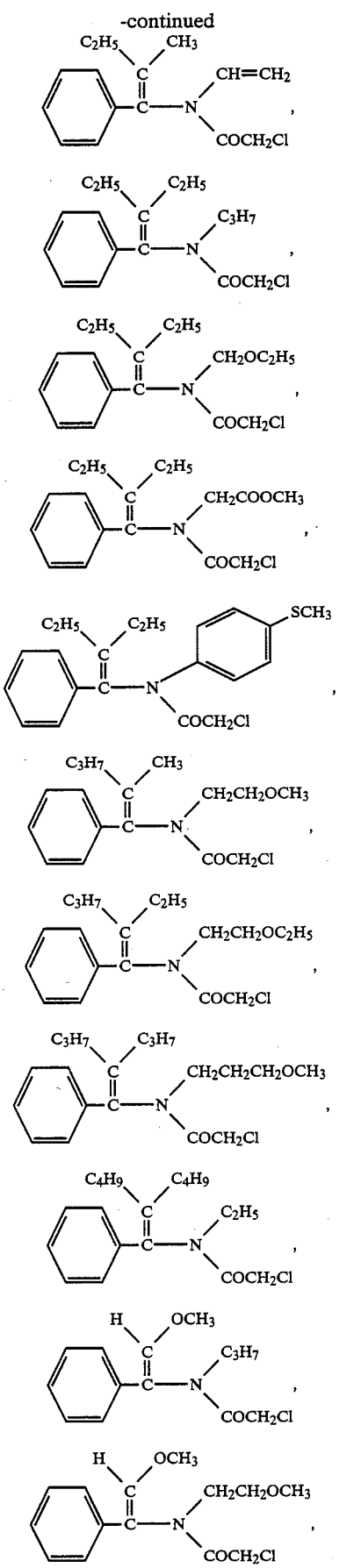
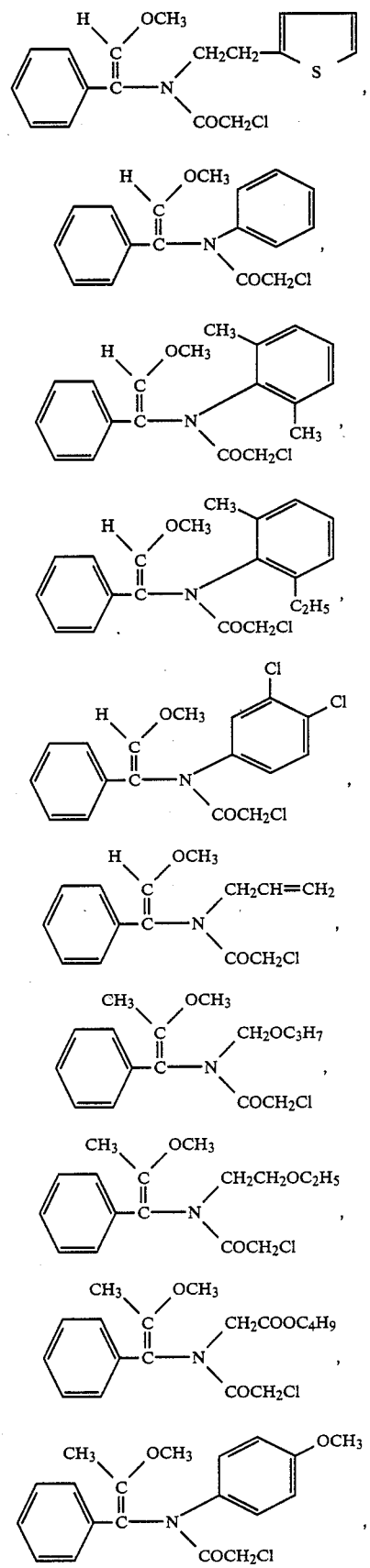

-continued
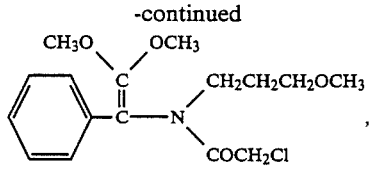,
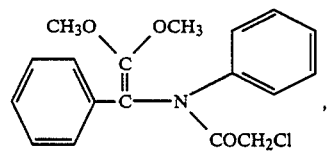,
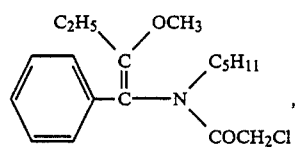,
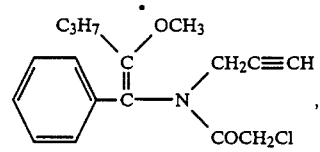,
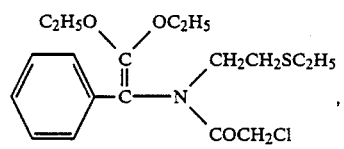,
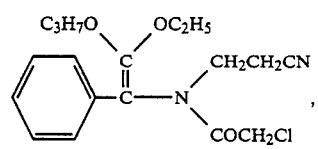,
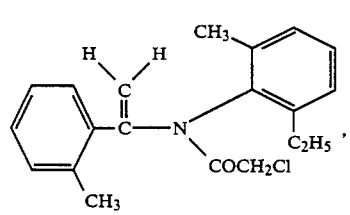,
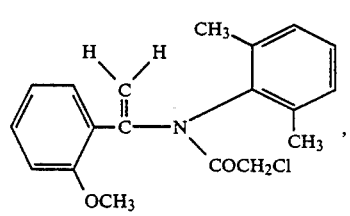,
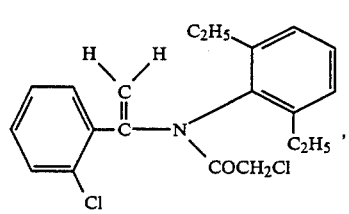,
-continued
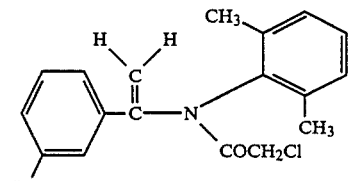,
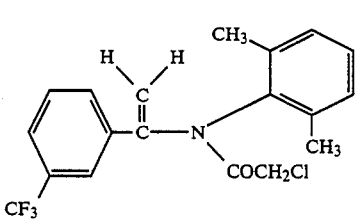,
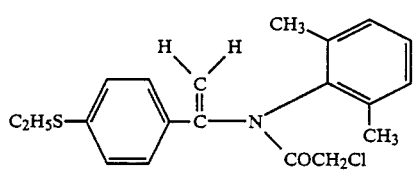,
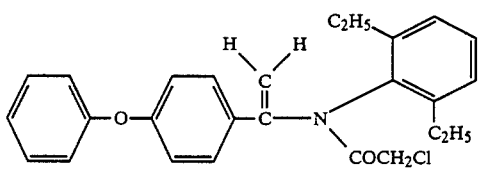,
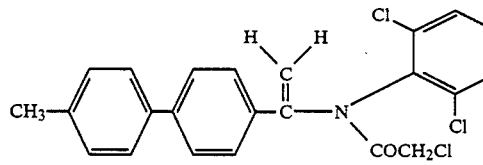,
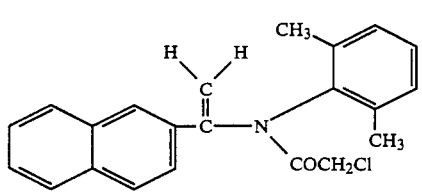,
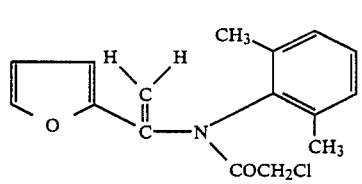,
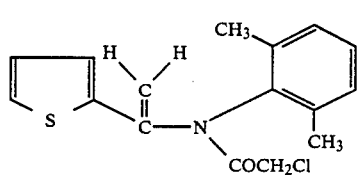,

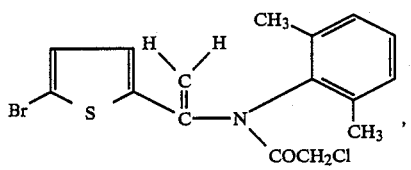,
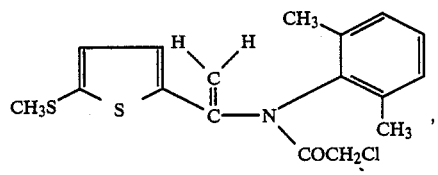,
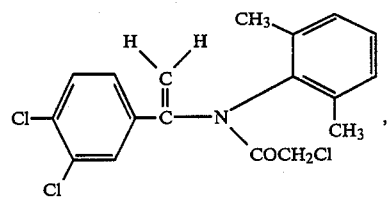,
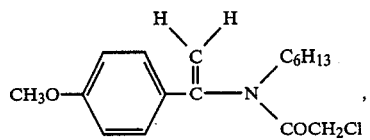,
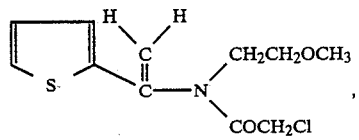,
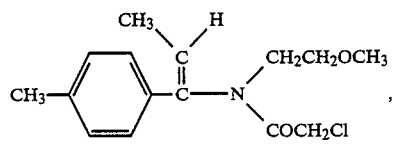,
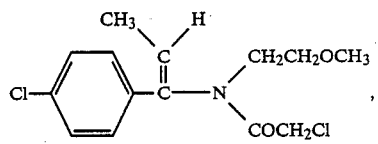,
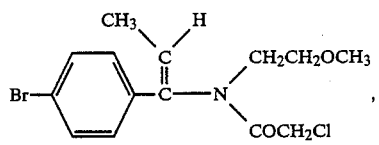,
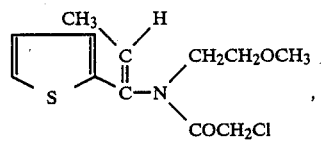,
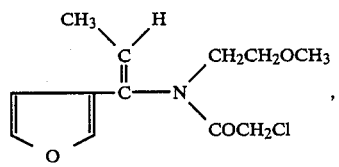,
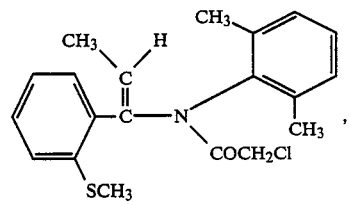,
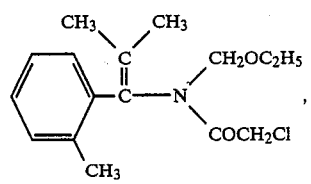,
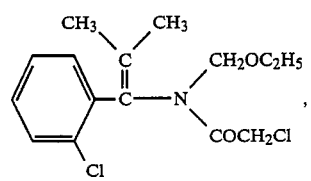,
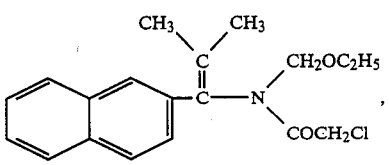,
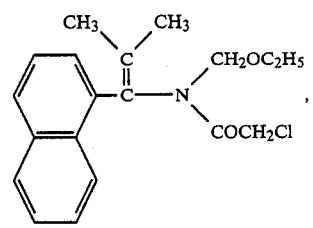,
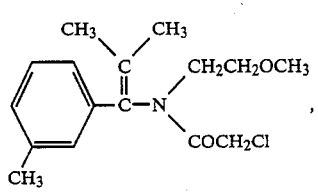,
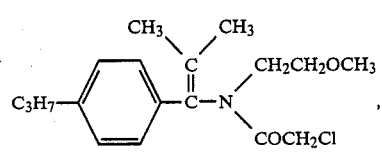,
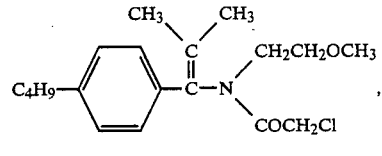,
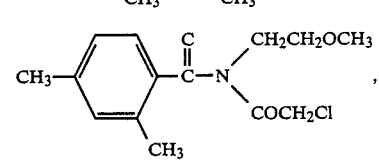,

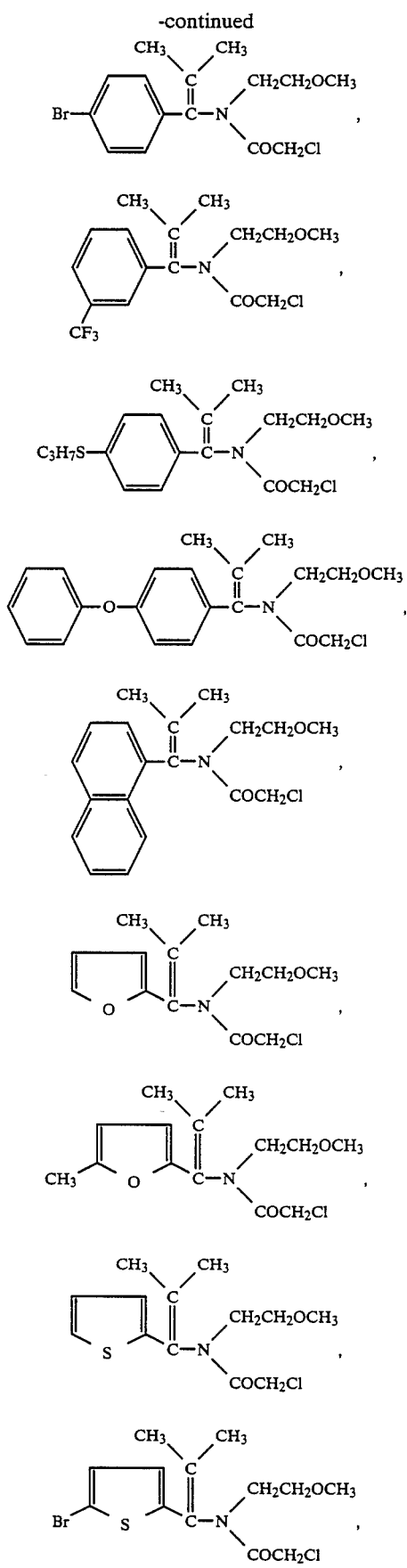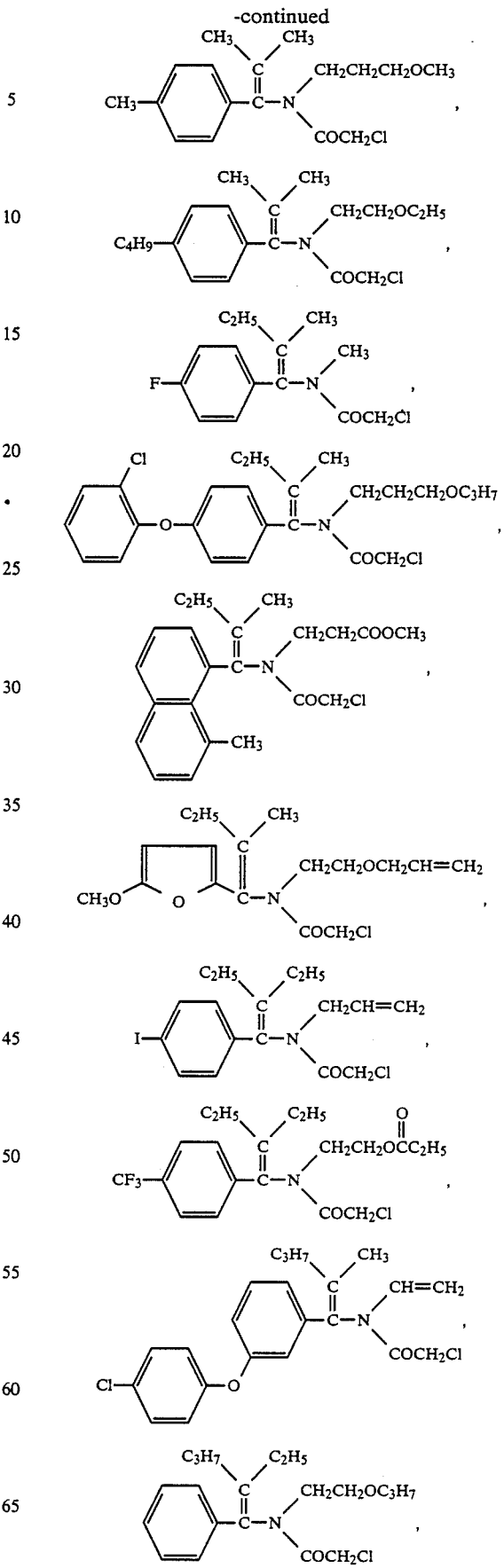

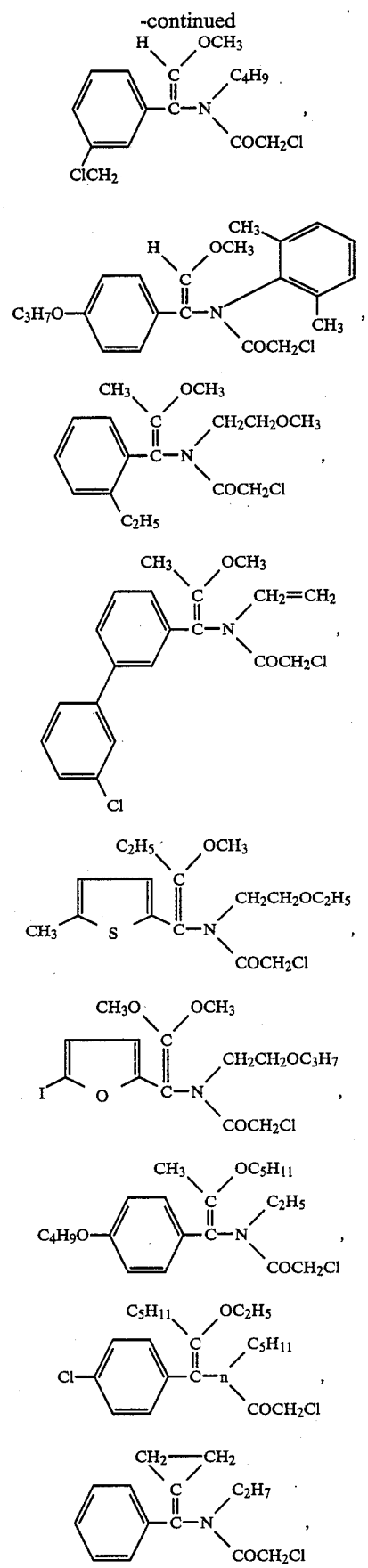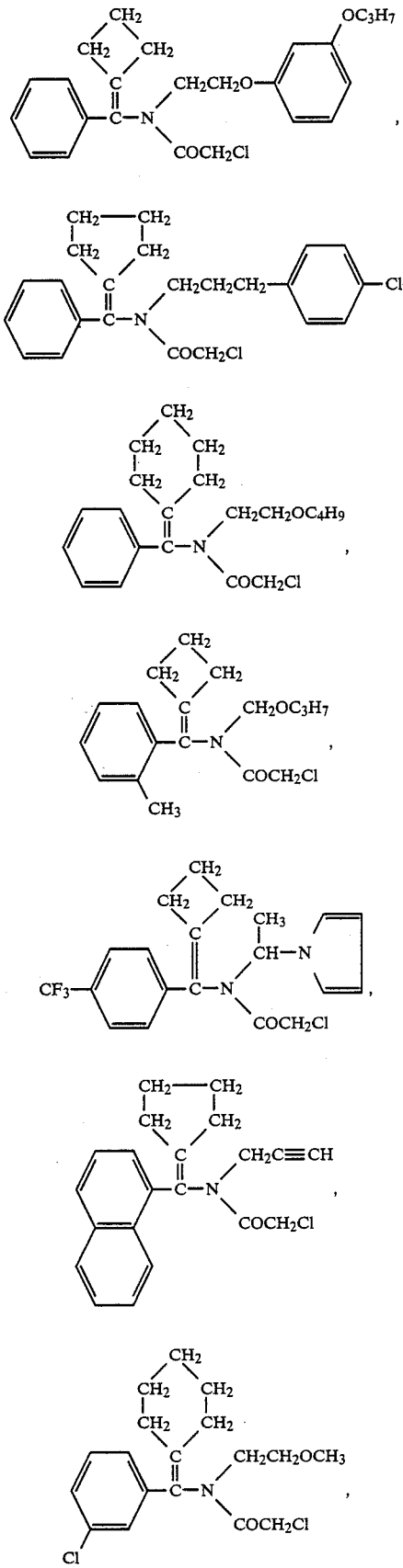

-continued
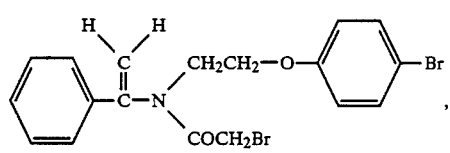
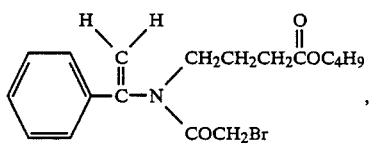
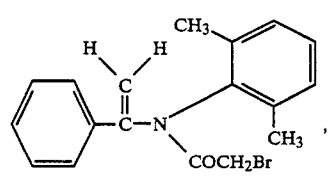
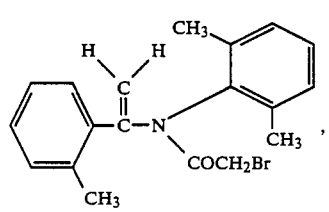
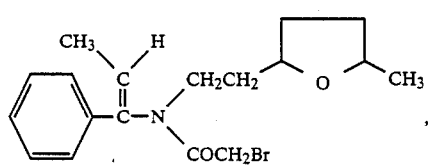
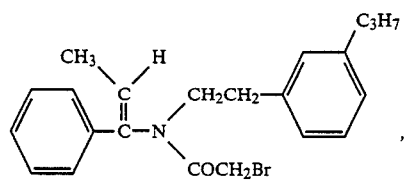
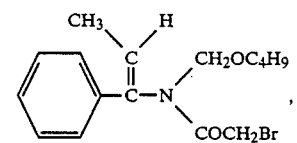
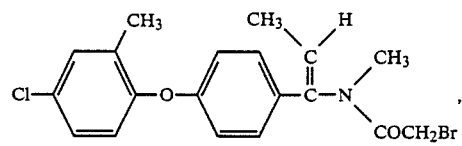
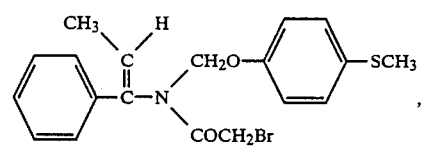
-continued
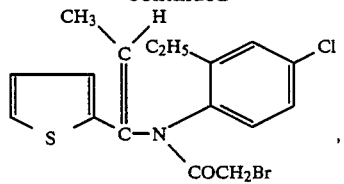
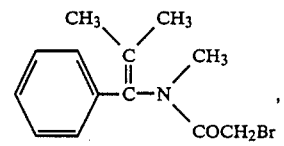
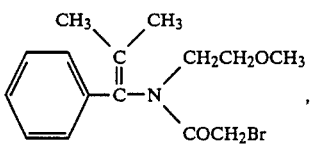
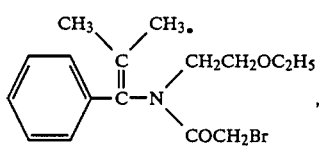
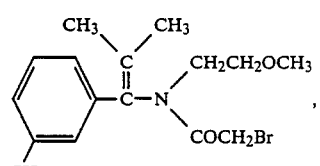
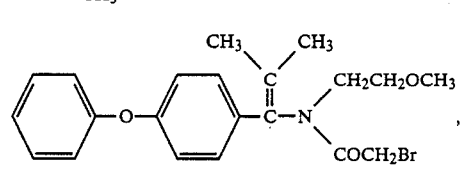
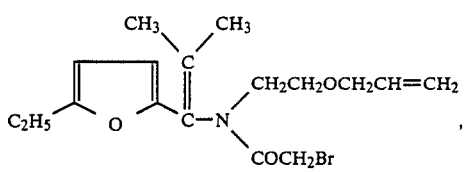
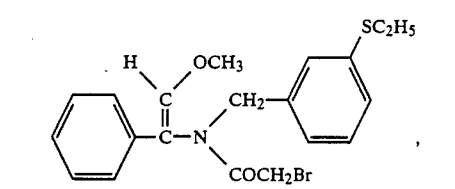
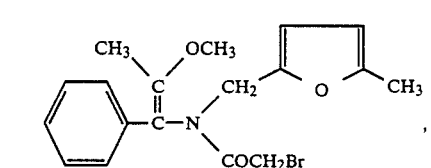
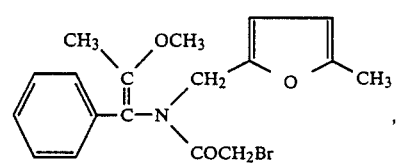

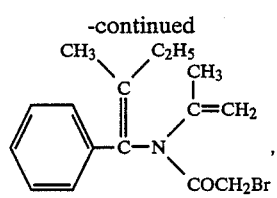
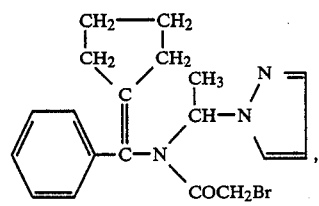
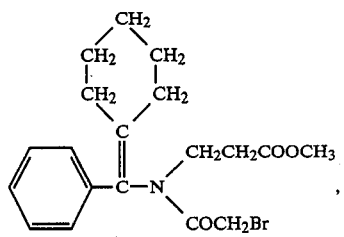
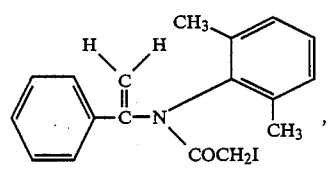
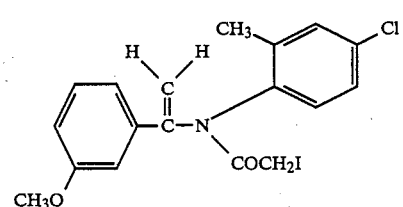
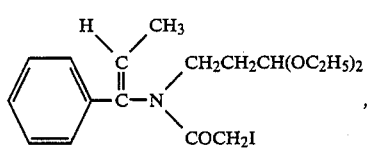
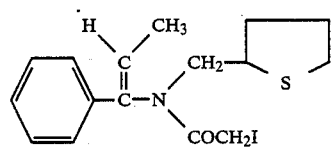
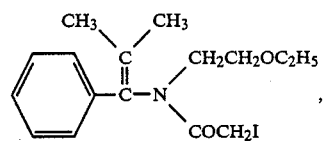
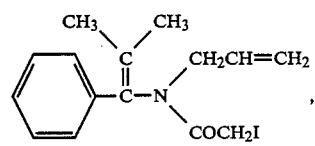
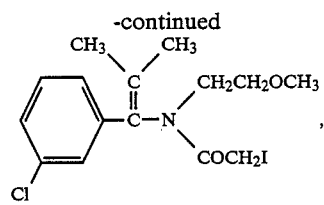
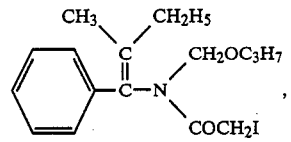
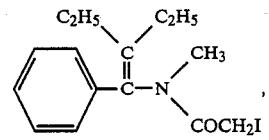
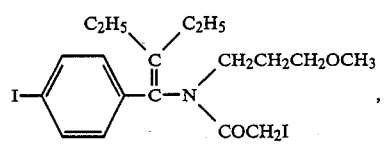
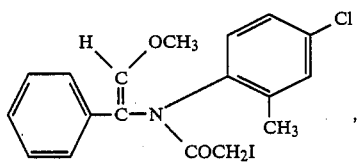
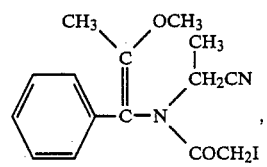
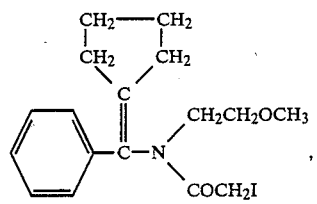
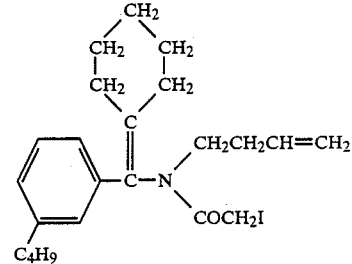
The compounds of general formula (I) may be produced typically by the following processes, for example.
(i) A process for producing the compound of general formula (I), which comprises reacting a Schiff base compound represented by the general formula

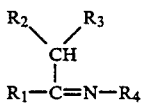 (II)

wherein $R_1$, $R_2$, $R_3$ and $R_4$ are as defined above, with a haloacetyl halogenide represented by the general formula

YCH$_2$COX wherein Y represents Cl, Br or I, and X represents Cl, Br, I or F.

The starting Schiff base compound of general formula (III) may be those which are prepared by any methods. For example, they can be obtained by dehydrocondensing the corresponding carbonyl compounds with amine compounds in accordance with the following reaction scheme.

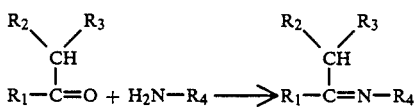

The mole ratio of the Schiff base compound of general formula (II) and the haloacetyl halogenide in the above reaction may be properly determined as required. For example, the haloacetyl halogenide is used generally in an equimolar proportion or a slightly excessive molar proportion.

Since hydrogen halide forms as a by-product in the above reaction, it is preferred to carry out the reaction usually in the copresence of a hydrogen halide scavenger. The scavenger may, for example, be triethylamine, tripropylamine, pyridine, sodium alcoholates or sodium carbonate.

In the above reaction, the use of an organic solvent is generally preferred. Examples of suitable organic solvents used in this reaction include benzene, toluene, xylene, hexane, petroleum ether, chloroform, methylene chloride, ethyl ether, dioxane, tetrahydrofuran, acetone, methyl ethyl ketone, acetonitrile, N,N-dimethylformamide, hexamethylphosphoramide and dimethyl sulfoxide.

The use of a basic polar solvent such as N,N-dimethylformamide, N,N-dimethylacetamide or hexamethylphosphoramide as the solvent for the reaction is preferred since in many cases, the reaction in such a solvent proceeds easily without the presence of a scavenger for the by-product hydrogen halide, and the final haloacetamide compound can be obtained in high yields.

The sequence of adding the starting materials in the above reaction is not particularly limited. For example, the Schiff base compound of general formula (II) is dissolved in a solvent, and the haloacetyl halogenide is added to the solution with stirring.

The reaction temperature may be selected from a broad range, and is, for example, $-20°$ to $150°$ C., preferably $-10°$ to $120°$ C. The reaction time varies depending upon the types of the starting materials and the reaction temperature. For example, it is 5 minutes to 10 days, preferably 1 hour to 50 hours. Preferably, the reaction is carried out with stirring.

There is no particular limitation on the method of isolating the final compound of general formula (I) from the reaction mixture and purifying it, and any known methods can be used. For example, the final compound can be obtained by distilling off the reaction solvent and the hydrogen halide scavenger after the reaction, adding water to the residue, extracting the mixture with an extracting organic solvent such as benzene, ether or chloroform, drying the organic layer with a desiccant such as sodium sulfate or calcium chloride, distilling off the solvent, and vacuum distilling the residue. Purification can also be carried out by chromatography, recrystallization, etc.

The use of an amide-type polar solvent such as N,N-dimethylformamide as the reaction solvent often obviates the need for the hydrogen halide scavenger. After the reaction, low-boiling materials are distilled off, and then by simply vacuum-distilling the residue, the final compound can be obtained. Alternatively, after the reaction, water is added to the reaction mixture, and the mixture is extracted with an extracting organic solvent such as benzene, ether or chloroform. The organic layer is dried with a desiccant such as sodium sulfate. The solvent is distilled off, and the residue is purified by vacuum distillation chromatography, or recrystallization to obtain the final compound.

(ii) The haloacetamide compound of general formula (I) can also be produced by a process which comprises reacting a Schiff base compound represented by the general formula

 (III)

wherein $R_1$, $R_2$ and $R_3$ are as defined above, and $R_8$ and $R_9$ are identical or different and each represents a hydrogen atom or is the same as $R_4$ except that the largest number of carbon atoms is less than that of $R_4$ by one, with a haloacetyl halogenide of the general formula

YCH$_2$COX wherein Y and X are as defined hereinabove, in the presence or absence of a silane compound represented by the following formula

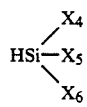

wherein $X_4$, $X_5$ and $X_6$ are identical or different and each represents a hydrogen atom or a halogen atom.

In the above reaction, the reaction temperature is, for example, $20°$ to $150°$ C., and the reaction time is 5 minutes to 10 days. As required, the reaction may be carried out in a suitable solvent same as the solvents illustrated with regard to the reaction (i), such as benzene, toluene, acetonitrile and chloroform.

When the above reaction is used in the absence of the silane compound, it is preferred to carry out the reaction in the presence of a known hydrogen halide scavenger in the reaction system.

(iii) The haloacetamide compound of general formula (I) can also be produced by a process which comprises reacting the Schiff base compound of general formula (III) above wilth a haloacetyl halogenide represented by the general formula

YCH$_2$COX wherein Y and X are as defined above, and threreafer reacting the product with a compound represented by the following formula

A—R$_{10}$ wherein A represents a hydrogen atom, a lithium atom, a sodium atom, a potassium atom, a zinc atom, or a (trialkyl)silyl group having 1 to 4 carbon atoms, and R$_{10}$ is the same as the substituent in the substituted alkyl group for R$_4$.

The use of an organic solvent is preferred in this reaction. Examples of the organic solvent are benzene, toluene, hexane, methylene chloride, chloroform, acetonitrile, ethyl ether, N,N-dimethylformamide and dimethyl sulfoxide. Where A in the above formula A—R$_{10}$ is a hydrogen atom, it is preferred to use a known hydrogen halide scavenger such as triethylamine, pyridine, sodium carbonate and potassium carbonate. In the above reaction, it is preferred to employ a reaction temperature of, for example, $-20°$ to $150°$ C. and a reaction period of, for example, 5 minutes to 10 days.

The compounds of general formula (I) provided by this invention exhibit an excellent efficacy as a herbicide, for example in pre-emergence and post-emergence soil treatment of gramineous weeds, broad-leaved weeds and perennial weeds. In particular, they exhibit a selective herbicidal effect when used as a herbicide for upland farms, and can therefore be applied to not only broad-leaved crops such as soybean, cotton and beet but also gramineous crops such as wheat, barley, corn and dry land rice. They also have excellent selective herbicidal activity on lawn. Compounds of general formula (I) which have a specific skeleton also exhibit a goods elective herbicidal effect against paddy weeds.

By properly selecting R$_1$, R$_2$, R$_3$, R$_4$ and Y in general formula (I), the compounds of the present invention exhibit an excellent herbicidal effect as herbicides for upland farms, lawn and paddies. Examples of weeds to which the compounds of this invention can be applied with especially good results include upland farm weeds and lawn eeds such as large crabgrass (*Digitaria ciliaris* Koeler), goosegrass (*Eleusine indica*), green foxtail (*Setaria viridis* Beauvois), common lamb's quarters (*Chenopodium album* L.), smartweed (*Polygonum longisetum* De. Bruyn.), large smartweed (*polygonum lapathifolium* L. subsp. nodosum (Pers.) Kitam), yellow nutsedge (*Cyperus microiria* Steud.), yellow cyperus (*Cyperus iria* L.), pigweed (*Amaranthus lividus* L.), common purslane (*Portulaca oleracea* L.), red clover (*Trfifolium pratense* L.), creeping woodsorrel (*Oxalis corniculata* L.), water foxtail (*Alopecurus aequalis* Sorol.), annual bluegrass (*Poa annua* L.), bedstraw (*Galium spurium* L.), blue morning glory (*Ipomoea indica* Merrill), "kawaraketsumei" (*Cassia nomame* Honda), common vetch (*Vicia sativa* L.), and shepherd's purse (*Capsella bursa-pastoris* Medik.) hairy beggartics (*Bidens pilosa*); paddy weeds such as barnyard grass (*Echinochloa crus-galli* Beauv.; *Echinochloa oryzicola* Vasing), umbrella plant (*Cyperus difformis* L.), three-square grass (*Scirpus juncoides* Rxb.), "mizugayatsuri" (*Cyperus serotinus* Rottr.), "himekugu" (*Hyllinga brevifolia* Rottr.), water chestnut (*Eleocharis kuroguwai* Ohwi), slender spikerush (*Eleocharis acicularis*, Roem. et Schult.), river bulrush (*Scirpus planiculmis* Fr. Schm.), arrowhead (*Sagittaria trifolia* L.), "aginashi" (*Sagittaria aginashi* Makino), narrowleaf waterplantain (*Alisma canaliculatum*, A. Bn. et Couche), "urikawwa" (*Sagittaria pygmaea* Miq.), largeleaf pondweed (*Potamogeton distinctus* A. Benn.), dropwort (*Oenanthe javanica* de Candolle), monochoria (*Monochoria vaginalis* Presl.), "ibokusa" (*Aneilema keisak* Hand-Mazt.), water wort (*Elatine triandra* Schk.), "himemisohagi" (*Ammannia multiflora* Roxb.), false loosestrife (*Ludwigia prostrata* Roxb.), "azemushiro" (*Lobelia chinensis* Lour.), burmarigold (*Bidens tripartita* L.), devil's beggarticks (*Bidens frondosa* L.), "abunome" (*Dopatrium junceum* Hamilt.), false pimpernel (*Lindernia pyxidaria* L.), and "azetogarashi" (*Vandellia angustifolia* Bentham).

Those haloacetamide compounds of general formula (I) which have a particularly excellent herbicidal effect and can be easily produced industrially are, for example, those of general formula (I) in which R$_1$ is an unsubstituted phenyl group, or a phenyl group substituted by a C$_1$-C$_6$ alkyl group, a C$_1$-C$_6$ alkoxy group, or a phenoxy group; R$_2$ and RHD 3 each represent a hydrogen atom or a C$_1$-C$_4$ alkyl group; and R$_4$ is a C$_1$-C$_6$ alkyl group, a C$_1$-C$_6$ alkoxyalkyl group, or a phenyl group substituted by a C$_1$-C$_4$ alkyl group and/or a C$_1$-C$_4$ alkoxy group. Typical examples of the above compounds include the following.

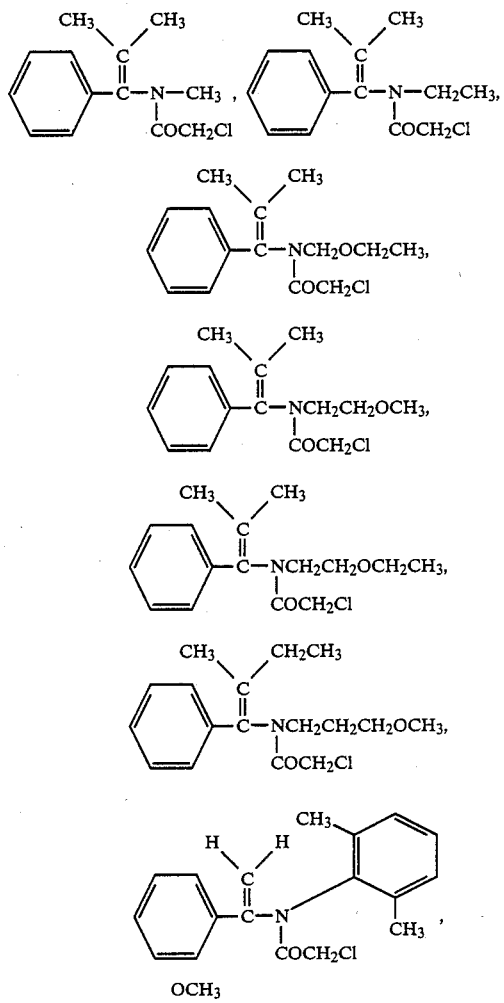

-continued

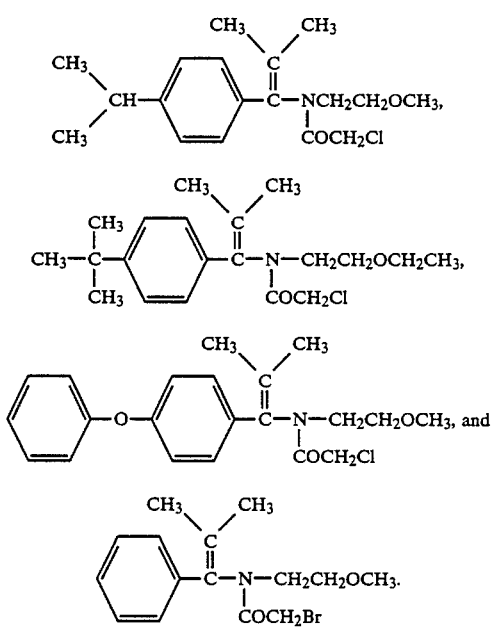

As a herbicide, the compound of general formula (I) exhibits a sufficient herbicidal efficacy when used at a rate of generally 2 to 3000 g/10 ares, preferably 10 to 1000 g/10 ares, more preferably 30 to 600 g/10 ares.

The compound of general formula (I) is frequently used conveniently in admixture with a known herbicide such as phenoxy-type compounds, triazine-type compounds, amide-type compounds, pyrazolate-type compounds, sulfonylurea-type compounds, etc. because the combined use permits a decrease in the amounts of the respective compounds and is moreover expected to produce a synergistic effect.

Since the compounds of general formula (I) affect the growth of vegetation, they can also be used as a defoliant, a germination inhibitor and a growth regulator.

The mode of using the compounds of general formula (I) may be those in which known herbicides are used. For example, they may be formulated into suitable forms such as granules, a dust, an emulsifiable concentrate, a wettable powder, tablets, an oil, an aerosol or a fumigant by using agriculturally acceptable solid or liquid diluents or carriers. As required, agriculturally acceptable adjuvants such as stickers, diluents, surfactants, dipsersants and solvents may also be incorporated. Such a herbicidal composition may contain a herbicidally effective amount, for example about 0.1 to about 90%, of the compound of general formula (I).

The compounds of general formula (I) in accordance with this invention can also be used in admixture with insecticides, fungicides, other agricultural chemicals, fertilizer materials, soil coditioners, etc.

Thus, according to this invention, there is provided a herbicidal composition comprising a herbicidally effective amount of the haloacetamide compound represented by general formula (I) and an agriculturally acceptable diluent or carrier.

There is further provided in accordance wiht this invention a method of controlling the growth of undesired vegetation which comprises applying an effective amount of the haloacetamide compound of general formula (I) to the locus to b protected from the undesired vegetation.

The following examples illustrate the present invention more specifically. It should be understood that the invention is in no way limited to these examples alone.

EXAMPLE 1

N-(1-methylbenzylidene)-2',6'-dimethylaniline (4.57 g; 0.020 mole) was dissolved in 25 ml of N,N-dimethylformamide (DMF for short). With stirring at room temperature, a solution of 2.48 g (0.022 mole) of chloroacetyl chloride in 5 ml of DMF was gradually added. The mixture was stirred for a while at room temperature, and then heated at 60° for 2 hours. The reaction solution was cooled to room temperature, and washed twice with 100 ml of ether. The organic layer was extracted with 100 ml of ether. The ethereal layer was dried over sodium sulfate, and then ether was distilled off. The resulting solid was recrystallized from a mixture of benzene and hexane to give 4.34 g of colorless crystals having a melting point of 91° to 92° C.

The infrared absorption spectrum of the colorless crystals was measured, and is shown in FIG. 1. The infrared absorption spectrum chart showed an absorption based on the C—H at 3100–2900 cm$^{-1}$ assigned to the C—H bond, a strong absopriton at 1680 cm$^{-1}$ assigned the carbonyl linkage of the amide group, and a weak absorption at 1615 cm$^{-1}$ assigned to the >C=C< bond.

The mass spectrum of the product showed a molecular ion peak (M⊕) at m/e 299, a peak corresponding to M⊕-Cl at m/e 264, and a peak corresponding to M⊕-COCH$_2$Cl at m/e 222.

The $^1$H-nuclear magnetic resonance spectrum (δ, ppm: tetramethylsilane as an internal standard, deuterochloroform as a solvent) of the product was measured, and the results are shown in FIG. 2. The results of its analysis were as follows:

| | | |
|---|---|---|
| | (a), (b) | 4.41, 4.97 ppm (2H) |
| | (c) | 3.75 ppm (s, 2H) |
| | (d) | 2.30 ppm (s, 6H) |
| benzene ring | | 7.10–7.60 ppm (8H) |

The elemental analysis of the product showed C72.08%, H5.98%, and N4.80%; which well agreed with the calculated values for the composition formula C$_{18}$H$_{18}$NClO (299.80), which were C71.11%, H6.05% and N4.67%.

The above results led to the determination that the isolated product was N-(1-phenyl)ethenyl-N-chloroaceto-2',6'-dimethylanilide. The yileld was 71%. This compound is designated as compound No. 1.

EXAMPLE 2

N-(ethoxymethylidene)-(1-phenyl-2,2-dimethylethenyl)amine (1.12 g; 0.0055 mole) was dissolved in 15 ml of benzene, and with stirring under cooling, a solution of 0.80 g (0.0071 mole) of chloroacetyl chloride and 1.02 g (0.0075 mole) of trichlorosilane in 5 ml of benzene was gradually added dropwise. The mixture was stirred overnight at room temperature, and neutralized with an aqueous solution of potassium carbonate under ice cooling. The organic layer was extracted with ether, and dried over sodium sulfate. The low-boiling components were evaporated, and the resulting yellow liquid was purified by column chromatography (silica gel) to give 0.71 g of a pale yellow viscous liquid.

The infrared absorption spectrum of the resulting compound showed an absorption at 3100 to 2800 cm$^{-1}$ assigned to the C—H bond, a strong absorption at 1680 cm$^{-1}$ assigned to the >C=O linkage of the amide, and an absorption based at 1600 cm$^{-1}$ assigned to the >C=C< bond.

The mass spectrum of the product showed a molecular ion peak (M$^\oplus$) at m/e 281, a peak corresponding to M$^\oplus$-OC$_2$H$_5$ at m/e 236, and a peak corresponding to M$^\oplus$-CH$_2$OC$_2$H$_5$ at m/e 222.

The $^1$H-nuclear magnetic resonance spectrum ($\delta$, ppm: tetramethylsilane as an internal standard, deuterochloroform as a solvent) of the product was measured. The results of its anlaysis were as follows.

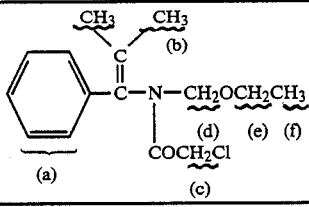

| | | | |
|---|---|---|---|
| (a) | 7.20 ppm | | (s, 5H) |
| (b) | 1.86 ppm | | (s, 6H) |
| (c) | 4.10 ppm | | (s, 2H) |
| (d) | 5.01 ppm, | 4.48 ppm | (d,d 2H) |
| (e) | 3.60 ppm | | (q, 2H) |
| (f) | 1.12 ppm | | (t, 3H) |

The elemental analysis values of the products were C64.10%, H7.09%, N5.01%, which well agreed with the calculated values for the composition formula C$_{15}$H$_{20}$NClO (281.78), which were C63.94%, H7.15%, N.4.97%.

The above results led to the determination that the isolated product was N-(1-phenyl-2,2-dimethyl)ethenyl-N-chloroaceto-ethoxymethylamide. The yield was 46%. The resulting compound is designated as compound No. 2.

EXAMPLE 3

N-(1-phenyl-2,2-dimethyl)ethylidene-2'-methoxyethylamine (2.06 g; 0.01 mole) was dissolved in 20 ml of DMF, and with stirring at room temperature, 1.52 g (0.013 mole) of chloroacetyl chloride was added gradually. The reaction solution was heated at 60° C. for 2 hours, then cooled to room temperature, and washed with water and an aqueous solution of sodium carbonate. The organic layer was extracted with ether. The ethereal layer was dried over sodium sulfate, and the ether was distilled off. The resulting viscous liquid was purified by column chromatography (silica gel) to give 1.90 g of a pale yellow viscous liquid.

The infrared absorption spectrum of the resulting compound showed an absorption at 3100 to 2800 cm$^{-1}$ assigned to the C—H bond, a strong absorption at 1670 cm$^{-1}$ assigned to the >C=O linkage of the amide, and an absorption at 1600 cm$^{-1}$ assigned to the >C=C< linkage.

The mass spectrum of the resultilng compound showed a molecular ion peak (M$^\oplus$) at m/e 281, a peak corresponding to M$^\oplus$-OCH$_3$ at m/e 266, and a peak corresponding to M$^\oplus$-Cl at m/e 246.

The $^1$H-nuclear magnetic resonance spectrum ($\delta$, ppm: tetramethylsilane as an internal standard, deuterochloroform as a solvent) of the resulting compound was measured. The results of analysis were shown below.

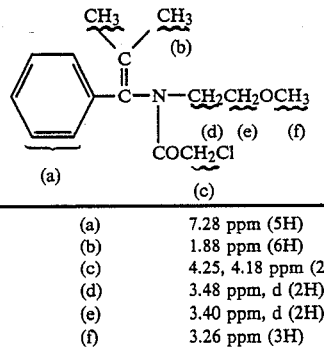

| | | |
|---|---|---|
| (a) | 7.28 ppm | (5H) |
| (b) | 1.88 ppm | (6H) |
| (c) | 4.25, 4.18 ppm | (2H) |
| (d) | 3.48 ppm, d | (2H) |
| (e) | 3.40 ppm, d | (2H) |
| (f) | 3.26 ppm | (3H) |

The elemental analysis values of the product were C63.83%, H7.21%, N5.12%, which well agreed with the calculated values for the composition formula C$_{15}$H$_{20}$NClO (281.78), namely C63.94%, H7.15%, N4.97%.

The above results led to the determination that the isolated product was N-[1-(phenyl)-2,2-(dimethyl)-ethenyl]-N-chloroaceto-2'-methoxyethylamide. The yield of the product was 67%. The resulting compound is designated as compound No. 3.

EXAMPLE 4

A solution of 1.12 g (0.0099 mole) of chloroacetyl chloride in 5 ml of benzene was gradually added dropwise with stirring under cooling to a solution of 1.29 g (0.0074 mole) of N-vinyl-(1-phenyl-2,2-dimethylethenyl)amine in 10 ml of benzene. The mixture was stirred for 30 minutes under ice cooling, and then 1.41 g (0.010 mole) of N-trimethylsilylpyrazole was added dropwise. The mixture was then stirred overnight at room temperature. The reaction mixture was washed with water, and the organic layer was extracted with benzene. The benzene layer was dried over sodium sulfate, and low-boiling components were removed. The resulting yellow viscous liquid was purified by column chromatography (silica gel) to give 1.00 g of colorless crystals.

The infrared absorption spectrum of the resulting compound showed an absorption at 3200 to 2800 cm$^{-1}$ assigned to the C—H bond and a strong absorption at 1665 cm$^{-1}$ assigned to the >C=O linkage of the amide.

The mass spectrum of the product showed a molecular ion peak (M$^\oplus$) at m/e 318, a peak corresponding

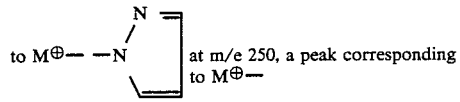

-continued

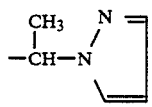 at m/e 222, and a peak corresponding to

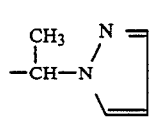 at m/e 95.

The ¹H-nuclear magnetic resonance spectrum (δ, ppm: tetramethylsilane as an internal standard, deuterochloroform as a solvent) was measured. The results of its analysis are shown below.

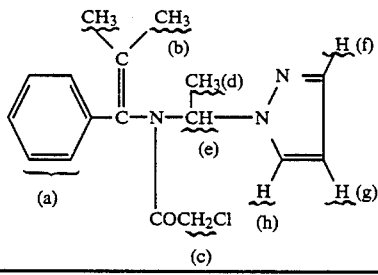

| | | |
|---|---|---|
| (a) | 7.29 ppm | (s, 5H) |
| (b) | 1.47 ppm | (d, 6H) |
| (c) | 4.38 ppm, | 4.00 ppm (dd, 2H) |
| (d) | 1.27 ppm | (d, 3H) |
| (e) | 6.93 ppm | (q, 1H) |
| (f) | 7.60 ppm | (d, 1H) |

-continued

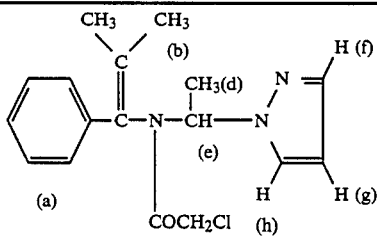

| | | |
|---|---|---|
| (g) | 6.19 ppm | (m, 1H) |
| (h) | 7.42 ppm | (d, 1H) |

The elemental analysis values of the product were C64.41%, H6.29%, N12.98%, which well agreed with the calculated values for the composition formula $C_{17}H_{20}N_3ClO$ (317.81), namely C64.24%, H6.34%, N13.22%.

The above results led to the determination that the isolated product was N-[1-(phenyl)-2,2-(dimethyl)-ethenyl]-N-chloroaceto-[1'-(1''-pyrazolyl)ethyl]amide. The yield was 42%. The resulting product is designated as compouind No. 4.

EXAMPLE 5

Various chloroacetamide compounds were synthesized as in Examples 1 to 4. Table 1 summarizes the appearances, the boiling points or melting points, the characteristic absorptions in infrared absorption spectra, and the elemental analysis values of the synthesized compounds. $R_1$, $R_2$, $R_3$ and $R_4$ in the table correspond to $R_1$, $R_2$, $R_3$ and $R_4$ in the following formula.

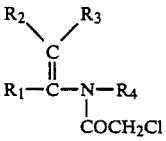

The boiling points in Table 1 were measured under reduced pressure (mmHg), and are indicated with the omission of mmHg, for example as 153° C./0.9 (=153° C./0.9 mmHg).

TABLE 1

| Compound No. | R₁ | R₂ | R₃ | R₄ | Appearance | bp. or mp. | IR (cm⁻¹) (c=o) | Elemental analysis values (%) (calculated values in the parentheses) | | |
|---|---|---|---|---|---|---|---|---|---|---|
| 5 | 4-CH₃O-phenyl | H | H | -(CH₂)₅CH₃ | Yellow viscous liquid | Purified on a column | 1660 | C 65.78 (65.90) | H 7.69 (7.81) | N 4.79 (4.52) |
| 6 | phenyl | H | H | -(CH₂)₂OCH₃ | Yellow viscous liquid | bp. 153° C./0.9 | 1660 | C 61.30 (61.54) | H 6.40 (6.36) | N 5.75 (5.52) |
| 7 | 2-methylthiophene | H | H | -CH₂CH₂OCH₃ | Brown liquid | Purified on a column | 1670 | C 50.73 (50.86) | H 5.21 (5.43) | N 5.16 (5.39) |
| 8 | phenyl | H | H | -(CH₂)₇OCH₃ | Yellow viscous liquid | bp. 162° C./0.9 | 1660 | C 62.62 (62.80) | H 6.88 (6.78) | N 5.44 (5.23) |
| 9 | phenyl | H | H | -CH(CH₃)-phenyl | Brown viscous liquid | mp. 64° C. | 1675 | C 72.00 (72.11) | H 5.93 (6.05) | N 4.60 (4.67) |
| 10 | phenyl | H | H | -CH₂-(tetrahydrofuran-2-yl) | Yellow viscous liquid | Purified on a column | 1675 | C 64.28 (64.40) | H 6.45 (6.49) | N 5.02 (5.01) |
| 11 | phenyl | H | H | phenyl | Pale yellow solid | mp. 103° C. | 1680 | C 70.51 (70.72) | H 5.11 (5.19) | N 5.23 (5.15) |
| 12 | phenyl | H | H | 2-methylphenyl | Yellow viscous liquid | bp. 170° C./0.4 | 1680 | C 71.30 (71.45) | H 5.76 (5.65) | N 5.11 (4.90) |

TABLE 1-continued

| Compound No. | R₁ | R₂ | R₃ | R₄ | Appearance | bp. or mp. | IR (cm⁻¹) (c = o) | Elemental analysis values (%) (calculated values in the parentheses) | | |
|---|---|---|---|---|---|---|---|---|---|---|
| 13 | phenyl | H | H | 2-OCH₃-phenyl | Pale yellow crystals | mp. 111° C. | 1665 | C 67.91 (67.66) | H 5.43 (5.34) | N 4.74 (4.64) |
| 14 | 2-CH₃-phenyl | H | H | 2,6-(CH₃)₂-phenyl | Pale pink crystals | mp. 76° C. | 1685 | C 72.50 (72.72) | H 6.39 (6.42) | N 4.67 (4.46) |
| 15 | 2-Cl-phenyl | H | H | 2,6-(CH₃)₂-phenyl | Pale yellow crystals | mp. 90° C. | 1700 | C 64.51 (64.68) | H 5.05 (5.13) | N 4.33 (4.19) |
| 16 | 4-Cl-phenyl | H | H | 2,6-(CH₃)₂-phenyl | White solid | mp. 117° C. | 1680 | C 64.04 (64.30) | H 5.56 (5.70) | N 4.31 (4.17) |
| 17 | 3-Br-phenyl | H | H | 2,6-(CH₃)₂-phenyl | Pale yellow crystals | mp. 112° C. | 1670 | C 56.88 (57.09) | H 4.53 (4.52) | N 3.90 (3.70) |

TABLE 1-continued

| Compound No. | R₁ | R₂ | R₃ | R₄ | Appearance | bp. or mp. | IR (cm⁻¹) (c=o) | Elemental analysis values (%) (calculated values in the parentheses) | | |
|---|---|---|---|---|---|---|---|---|---|---|
| 18 | 2-OCH₃-phenyl | H | H | 2,6-dimethylphenyl | Pale brown solid | mp. 97° C. | 1655 | C 69.14 (69.19) | H 6.07 (6.11) | N 4.41 (4.25) |
| 19 | 3,4-dichlorophenyl | H | H | 2,6-dimethylphenyl | Yellow crystals | mp. 110° C. | 1680 | C 58.64 (58.64) | H 4.41 (4.37) | N 4.08 (3.80) |
| 20 | 2-naphthyl | H | H | 2,6-dimethylphenyl | Brown crystals | mp. 111° C. | 1670 | C 75.64 (75.53) | H 5.79 (5.76) | N 4.19 (4.00) |
| 21 | tetrahydrofuran-2-yl | H | H | 2,6-dimethylphenyl | Brown viscous liquid | Purified on a column | 1680 | C 66.10 (66.32) | H 5.60 (5.57) | N 4.92 (4.83) |
| 22 | thiophen-2-yl | H | H | 2,6-dimethylphenyl | Brown viscous liquid | Purified on a column | 1680 | C 62.61 (62.84) | H 5.38 (5.27) | N 4.50 (4.58) |

TABLE 1-continued

| Compound No. | R₁ | R₂ | R₃ | R₄ | Appearance | bp. or mp. | IR (cm⁻¹) (c = o) | Elemental analysis values (%) (calculated values in the parentheses) | | |
|---|---|---|---|---|---|---|---|---|---|---|
| 23 | 5-bromo-2-methylthiophen-3-yl | H | H | 2,6-dimethylphenyl | Yellow viscous liquid | Purified on a column | 1680 | C 50.14 (49.95) | H 3.98 (3.93) | N 3.90 (3.64) |
| 24 | 1,2-dimethylpyrrol-3-yl | H | H | 2,6-dimethylphenyl | Pale brown solid | mp. 151° C. | 1670 | C 67.28 (67.43) | H 6.28 (6.32) | N 9.50 (9.25) |
| 25 | phenyl | H | H | 2-methyl-6-ethylphenyl (2,6-dimethyl/ethyl) | Pale yellow solid | mp. 78° C. | 1685 | C 72.60 (72.72) | H 6.25 (6.42) | N 4.41 (4.46) |
| 26 | phenyl | H | H | 2,6-diethylphenyl | Pale green crystals | mp. 55° C. | 1675 | C 73.50 (73.27) | H 6.83 (6.76) | N 4.47 (4.27) |
| 27 | phenyl | H | H | 2,6-dichlorophenyl | Yellow crystals | mp. 113° C. | 1695 | C 56.20 (56.42) | H 3.59 (3.55) | H 3.96 (4.11) |

TABLE 1-continued

| Compound No. | R₁ | R₂ | R₃ | R₄ | Appearance | bp. or mp. | IR (cm⁻¹) (c=o) | Elemental analysis values (%) (calculated values in the parentheses) | | |
|---|---|---|---|---|---|---|---|---|---|---|
| 28 | phenyl | H | H | naphthyl | Pale yellow crystals | mp. 107° C. | 1660 | C 74.55 (74.65) | H 4.92 (5.01) | N 4.45 (4.35) |
| 29 | phenyl | H | CH₃ | ‒(CH₂)₂OCH₃ | Yellow viscous liquid | bp. 154° C./0.6 | 1660 | C 62.59 (62.80) | H 6.76 (6.78) | N 5.34 (5.23) |
| 30 | phenyl | H | CH₃ | ‒(CH₂)₃OCH₃ | Yellow viscous liquid | Purified on a column | 1660 | C 63.67 (63.94) | H 7.22 (7.15) | N 5.09 (4.97) |
| 31 | phenyl | H | CH₃ | 2,6-dimethylphenyl | Yellow viscous liquid | bp. 155° C./0.3 | 1670 | C 72.52 (72.72) | H 6.35 (6.42) | N 4.66 (4.46) |
| 32 | phenyl | CH₃ | CH₃ | ‒CH₃ | Pale yellow viscous liquid | bp. 143-145° C./0.7 | 1675 | C 65.42 (65.68) | H 6.70 (6.78) | N 5.98 (5.89) |
| 33 | phenyl | CH₃ | CH₃ | ‒CH₂OCH₃ | Colorless solid | bp. 128-129° C./0.1 | 1680 | C 62.77 (62.80) | H 6.90 (6.78) | N 5.18 (5.23) |

TABLE 1-continued

| Compound No. | R₁ | R₂ | R₃ | R₄ | Appearance | bp. or mp. | IR (cm⁻¹) (c=o) | Elemental analysis values (%) (calculated values in the parentheses) | | |
|---|---|---|---|---|---|---|---|---|---|---|
| 34 | 3-CH₃-phenyl | CH₃ | CH₃ | —CH₂CH₂OCH₃ | Colorless viscous liquid | bp. 138–140° C./0.1 | 1660 | C 64.69 (64.97) | H 7.68 (7.50) | N 4.75 (4.74) |
| 35 | 4-(CH(CH₃)₂)-phenyl | CH₃ | CH₃ | —CH₂CH₂OCH₃ | Colorless viscous liquid | bp. 165–168° C./0.2 | 1660 | C 66.49 (66.76) | H 7.82 (8.09) | N 4.57 (4.32) |
| 36 | 4-Cl-phenyl | CH₃ | CH₃ | —CH₂CH₂OCH₃ | Pale yellow viscous liquid | bp. 172–174° C./0.2 | 1665 | C 56.73 (56.96) | H 6.23 (6.05) | N 4.47 (4.43) |
| 37 | 3,4-(CH₃O)₂-phenyl | CH₃ | CH₃ | —CH₂CH₂OCH₃ | Pale yellow viscous liquid | Purified on a column | 1665 | C 59.59 (59.73) | H 7.03 (7.08) | N 4.12 (4.10) |
| 38 | 2-thienyl | CH₃ | CH₃ | —CH₂CH₂OCH₃ | Pale yellow viscous liquid | Purified on a column | 1670 | C 54.02 (54.25) | H 6.49 (6.30) | N 4.88 (4.87) |
| 39 | phenyl | CH₃ | CH₃ | —CH₂CH₂OC₂H₅ | Pale yellow viscous liquid | bp. 145–146° C./0.17 | 1660 | C 64.78 (64.97) | H 7.63 (7.50) | N 4.70 (4.74) |
| 40 | phenyl | CH₃ | CH₃ | —CH₂CH₂OC₃H₇ | Pale yellow viscous liquid | bp. 154–156° C./0.20 | 1660 | C 65.67 (65.90) | H 7.53 (7.81) | N 4.44 (4.52) |

TABLE 1-continued

| Compound No. | R$_1$ | R$_2$ | R$_3$ | R$_4$ | Appearance | bp. or mp. | IR (cm$^{-1}$) (c = o) | Elemental analysis values (%) (calculated values in the parentheses) | | |
|---|---|---|---|---|---|---|---|---|---|---|
| 41 | phenyl | CH$_3$ | CH$_3$ | ─(CH$_2$)$_3$OCH$_3$ | Pale yellow viscous liquid | Purified on a column | 1660 | C 65.03 (64.97) | H 7.40 (7.50) | N 4.86 (4.74) |
| 42 | phenyl | CH$_3$ | CH$_3$ | ─CH(C$_2$H$_5$)CH$_2$OCH$_3$ | Pale brown viscous liquid | bp. 168-170° C./0.25 | 1665 | C 66.03 (65.90) | H 7.64 (7.81) | N 4.38 (4.52) |
| 43 | phenyl | CH$_3$ | CH$_3$ | ─(CH$_2$)$_3$SCH$_3$ | Pale yellow viscous liquid | Purified on a column | 1660 | C 61.42 (61.62) | H 7.14 (7.11) | N 4.50 (4.49) |
| 44 | phenyl | CH$_3$ | CH$_3$ | ─CH$_2$-(tetrahydrofuran-2-yl) | Pale yellow viscous liquid | Purified on a column | 1665 | C 66.18 (66.33) | H 7.16 (7.20) | N 4.71 (4.55) |
| 45 | phenyl | CH$_3$ | CH$_3$ | ─CH$_2$CH$_2$OCH$_2$CH═CH$_2$ | Pale yellow viscous liquid | bp. 161-163° C./0.21 | 1665 | C 66.25 (66.33) | H 7.24 (7.20) | N 4.59 (4.55) |
| 46 | phenyl | CH$_3$ | CH$_3$ | ─CH$_2$CH═CH$_2$ | Pale yellow viscous liquid | Purified on a column | 1670 | C 68.55 (68.31) | H 7.01 (6.88) | N 5.56 (5.31) |
| 47 | phenyl | CH$_3$ | CH$_3$ | phenyl | Pale yellow solid | mp. 77° C. | 1680 | C 71.88 (72.11) | H 5.92 (6.05) | N 4.63 (4.67) |

TABLE 1-continued

| Compound No. | R₁ | R₂ | R₃ | R₄ | Appearance | bp. or mp. | IR (cm⁻¹) (c = o) | Elemental analysis values (%) (calculated values in the parentheses) | | |
|---|---|---|---|---|---|---|---|---|---|---|
| 48 | phenyl | CH₃ | CH₃ | 2,6-dimethylphenyl (with 2-CH₃) | Pale yellow solid | mp. 118° C. | 1670 | C 73.30 (73.27) | H 6.76 (6.76) | N 4.39 (4.27) |
| 49 | phenyl | CH₃ | C₂H₅ | —CH₂CH₂OCH₃ | Pale yellow viscous liquid | bp. 150–152° C./0.23 | 1660 | C 64.79 (64.97) | H 7.57 (7.50) | N 4.74 (4.74) |

EXAMPLE 6

Various haloacetamide compounds were synthesized as in Examples 1 to 5. The structures of the compounds were determined by infrared absorption spectroscopy, mass spectroscopy, $^1$H-nuclear magnetic resotnance scpectroscopy and elemental analysis. Table 2 summarizes the substituents and elemental analysis values of the compounds. $R_1$, $R_2$, $R_3$, $R_4$ and Y in the table correspond to $R_1$, $R_2$, $R_3$, $R_4$ and Y in the following formula.

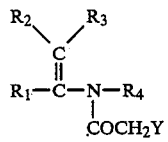

TABLE 2
| No. | R₁ | R₂ | R₃ | R₄ | Y | Elemental analysis values (%) (calculated values in the parentheses) | | |
|---|---|---|---|---|---|---|---|---|
| | | | | | | C | H | N |
| 50 | 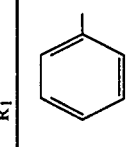 | H | H | —CH₂CH₂CH₃ | Cl | 66.40 (66.24) | 5.84 (5.99) | 5.91 (5.94) |
| 51 | 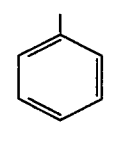 | H | H | —CH₂OC₄H₉ | Cl | 63.88 (63.94) | 7.12 (7.15) | 5.10 (4.97) |
| 52 | 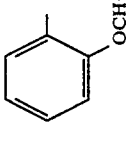 | H | H | —CH₂CH₂OCH₃ | Cl | 59.20 (59.26) | 6.43 (6.39) | 5.11 (4.94) |
| 53 | 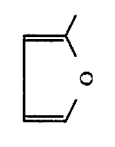 | H | H | —CH₂CH₂OCH₃ | Cl | 54.28 (54.21) | 5.83 (5.79) | 5.60 (5.75) |
| 54 | 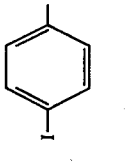 | H | H | ₊(CH₂)₇CN | Cl | 44.79 (44.74) | 4.02 (4.00) | 6.91 (6.96) |
| 55 | 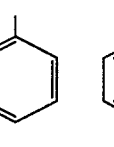 | H | H | —CH₂—⌬ | Cl | 71.30 (71.45) | 5.54 (5.64) | 4.98 (4.90) |
| 56 | 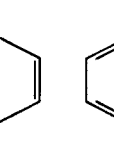 | H | H | —CH₂CH₂OCCH₂Cl (C=O) | Cl | 52.90 (53.18) | 4.77 (4.78) | 4.42 (4.43) |
| 57 | 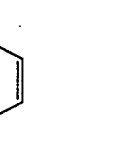 | H | H | —CH₂CH₂OCH₂CH=CH₂ | Cl | 64.50 (64.39) | 6.37 (6.48) | 5.00 (5.01) |

TABLE 2-continued
| No. | R₁ | R₂ | R₃ | R₄ | Y | Elemental analysis values (%) (calculated values in the parentheses) | | |
|---|---|---|---|---|---|---|---|---|
| | | | | | | C | H | N |
| 58 | 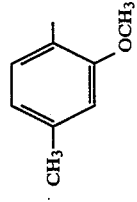 | H | H | 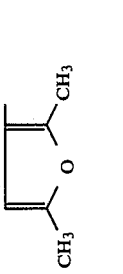 | Cl | 68.63 (68.46) | 5.67 (5.74) | 4.29 (4.44) |
| 59 | 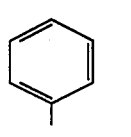 | H | H | 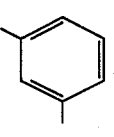 | Cl | 77.71 (77.52) | 4.70 (4.88) | 3.69 (3.77) |
| 60 | 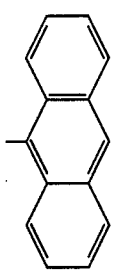 | H | H | 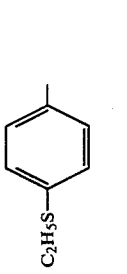 | Cl | 74.55 (74.67) | 6.90 (6.84) | 4.80 (3.96) |
| 61 | 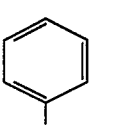 | H | H | 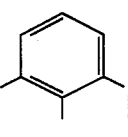 | Cl | 60.66 (60.80) | 5.24 (5.40) | 4.27 (4.17) |
| 62 | 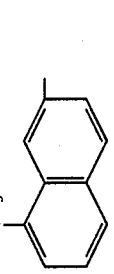 | H | H | 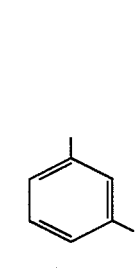 | Cl | 66.58 (66.74) | 6.20 (6.16) | 3.80 (3.89) |
| 63 | 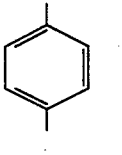 | H | H | 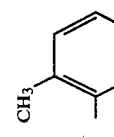 | Cl | 62.20 (62.04) | 4.50 (4.66) | 3.68 (3.81) |

TABLE 2-continued
| No. | R$_1$ | R$_2$ | R$_3$ | R$_4$ | Y | Elemental analysis values (%) (calculated values in the parentheses) | | |
|---|---|---|---|---|---|---|---|---|
| | | | | | | C | H | N |
| 64 | 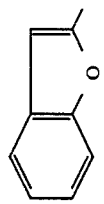 | H | H | 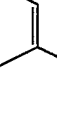 | Cl | 70.42 (70.69) | 5.28 (5.34) | 4.29 (4.12) |
| 65 | 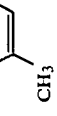 | H | H | 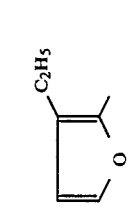 | Cl | 58.23 (58.02) | 5.21 (5.15) | 4.19 (3.98) |
| 66 | 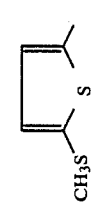 | H | H | 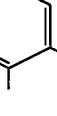 | Cl | 73.31 (73.27) | 6.69 (6.77) | 4.36 (4.27) |
| 67 | 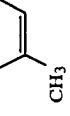 | H | H | 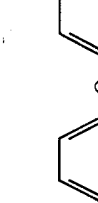 | Cl | 68.93 (68.77) | 6.81 (6.68) | 4.04 (4.22) |
| 68 | 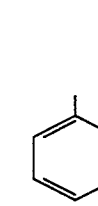 | H | H | 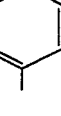 | Cl | 74.50 (74.36) | 6.18 (6.24) | 3.25 (3.34) |

TABLE 2-continued
| No. | R₁ | R₂ | R₃ | R₄ | Y | Elemental analysis values (%) (calculated values in the parentheses) | | |
|---|---|---|---|---|---|---|---|---|
| 69 |  | H | H | 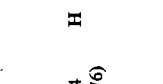 | Cl | C 64.24 (64.13) | H 4.18 (4.21) | N 3.18 (3.25) |
| 70 |  | H | H | 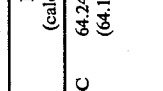 | Cl | C 63.94 (63.76) | H 4.68 (4.72) | N 4.41 (4.38) |
| 71 |  | H | H | 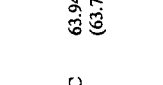 | Cl | C 56.28 (56.52) | H 4.70 (4.52) | N 3.25 (3.14) |
| 72 | 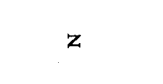 | H | H | —CH₂CH=CH₂ | Cl | C 66.23 (66.24) | H 6.02 (5.99) | N 5.87 (5.94) |
| 73 | 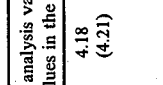 | H | —CH₃ | —C₃H₇ | Cl | C 55.34 (55.28) | H 5.19 (5.30) | N 4.82 (4.60) |
| 74 |  | H | —CH₃ | —C₄H₉ | Cl | C 67.61 (67.78) | H 7.57 (7.59) | N 5.37 (5.27) |
| 75 | 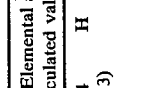 | H | —CH₃ | —CH₂OC₂H₅ | Cl | C 51.63 (51.40) | H 5.94 (5.97) | N 4.52 (4.61) |

TABLE 2-continued

| No. | R₁ | R₂ | R₃ | R₄ | Y | Elemental analysis values (%) (calculated values in the parentheses) | | |
|---|---|---|---|---|---|---|---|---|
| 76 | 4-CH₃-C₆H₄- | H | —CH₃ | —CH₂CH₂OCH₃ | Cl | C 63.69 (63.93) | H 7.18 (7.15) | N 4.98 (4.97) |
| 77 | 4-Cl-C₆H₄- | H | —CH₃ | —CH₂CH₂OCH₃ | Cl | C 55.77 (55.64) | H 5.70 (5.67) | N 4.74 (4.64) |
| 78 | 4-Br-C₆H₄- | H | —CH₃ | —CH₂CH₂OCH₃ | Cl | C 48.41 (48.50) | H 4.91 (4.94) | N 3.93 (4.04) |
| 79 | 4-C₃H₇S-C₆H₄- | H | —CH₃ | —CH₂CH₂OCH₃ | Cl | C 59.71 (59.72) | H 7.23 (7.08) | N 4.00 (4.10) |
| 80 | 2-furyl | H | —CH₃ | —CH₂CH₂OCH₃ | Cl | C 55.86 (55.92) | H 6.38 (6.26) | N 5.36 (5.44) |
| 81 | 5-methyl-2-thienyl | H | —CH₃ | —CH₂CH₂OCH₃ | Cl | C 52.88 (52.64) | H 6.17 (5.89) | N 5.16 (5.12) |
| 82 | 4-bromo-2-thienyl | H | —CH₃ | —CH₂CH(OCH₃)₂ | Cl | C 40.97 (40.80) | H 4.46 (4.48) | N 3.61 (3.66) |
| 83 | C₆H₅- | H | —CH₃ | —(CH₂)₃OCH(CH₃)₂ | Cl | C 65.75 (65.90) | H 7.59 (7.81) | N 4.60 (4.52) |
| 84 | C₆H₅- | H | —CH₃ | —CH(C₂H₅)CH₂OCH₃ | Cl | C 64.70 (64.96) | H 7.38 (7.50) | N 4.50 (4.74) |

TABLE 2-continued
| No. | R₁ | R₂ | R₃ | R₄ | Y | Elemental analysis values (%) (calculated values in the parentheses) | | | | | |
|---|---|---|---|---|---|---|---|---|---|---|---|
| 85 | 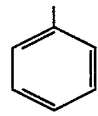 | H | —CH₃ | —CH₂CH₂O | Cl | C | 68.97 (69.19) | H | 6.08 (6.11) | N | 4.15 (4.25) |
| 86 | 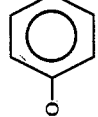 | H | —CH₃ | ─(CH₂)₃O─ | Cl | C | 58.72 (58.71) | H | 5.41 (5.20) | N | 3.68 (3.80) |
| 87 | 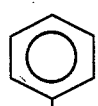 | H | —CH₃ | —CH₂─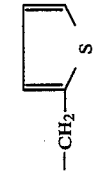 | Cl | C | 62.89 (63.05) | H | 5.14 (4.96) | N | 4.56 (4.60) |
| 88 | 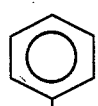 | H | —CH₃ | —CH₂COOC₂H₅ | Cl | C | 60.88 (60.91) | H | 6.15 (6.13) | N | 4.80 (4.74) |
| 89 | 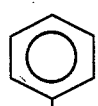 | H | —CH₃ | —CH₂CH₂OCCH₂Cl (O) | Cl | C | 54.55 (54.56) | H | 5.27 (5.19) | N | 4.28 (4.24) |
| 90 | 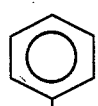 | H | —CH₃ | 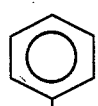 | Cl | C | 63.58 (63.76) | H | 4.70 (4.72) | N | 4.36 (4.38) |
| 91 | 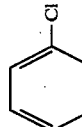 | H | —CH₃ | (2,6-dimethylphenyl) | Cl | C | 66.65 (66.74) | H | 6.08 (6.16) | N | 3.99 (3.89) |

TABLE 2-continued
| No. | R₁ | R₂ | R₃ | R₄ | Y | Elemental analysis values (%) (calculated values in the parentheses) | | |
|---|---|---|---|---|---|---|---|---|
| 92 |  | H | —CH₃ | 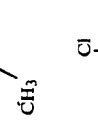 | Cl | C 64.64 (64.75) | H 6.03 (6.04) | N 4.39 (4.20) |
| 93 | 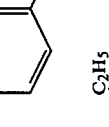 | H | —CH₃ |  | Cl | C 68.07 (68.12) | H 4.56 (4.63) | N 3.80 (3.78) |
| 94 | 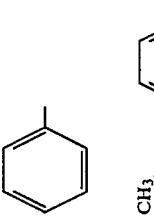 | H | —CH₃ | $\underset{\underset{C=CH_2}{|}}{C_2H_5}$ | Cl | C 63.77 (63.84) | H 5.80 (5.67) | N 4.35 (4.38) |
| 95 | 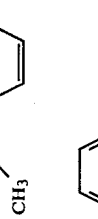 | H | —CH₃ | —CH₂CH=CH₂ | Cl | C 67.47 (67.33) | H 6.47 (6.46) | N 5.65 (5.61) |
| 96 | 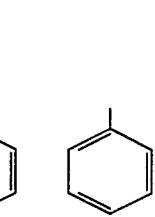 | H | —CH₃ | —CH₂CH=CH₂ | Cl | C 70.01 (69.97) | H 7.49 (7.60) | N 4.93 (4.80) |
| 97 | 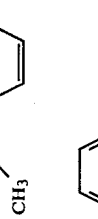 | H | —C₂H₅ | —CH₂CH₂OCH₃ | Cl | C 63.69 (63.94) | H 7.22 (7.15) | N 5.04 (4.97) |
| 98 | 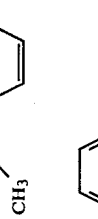 | H | —C₂H₅ | —CH₂CH₂OC₂H₅ | Cl | C 64.80 (64.97) | H 7.58 (7.50) | N (4.75) (4.74) |

TABLE 2-continued
| No. | R₁ | R₂ | R₃ | R₄ | Y | Elemental analysis values (%) (calculated values in the parentheses) | | |
|---|---|---|---|---|---|---|---|---|
| | | | | | | C | H | N |
| 99 | 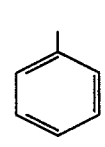 | H | —C₂H₅ | —(CH₂)₃SCH₃ | Cl | 61.49 (61.62) | 7.08 (7.11) | 4.36 (4.49) |
| 100 | 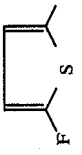 | H | —C₂H₅ | —CH₂CH₂— | Cl | 61.41 (61.44) | 5.60 (5.44) | 3.85 (3.98) |
| 101 | 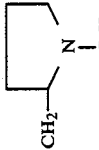 | H | —C₂H₅ |  | Cl | 68.20 (68.14) | 8.11 (8.13) | 8.17 (8.37) |
| 102 | 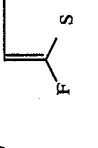 | H | —C₂H₅ | —(CH₂)₃OCH₂C≡CH | Cl | 67.48 (67.60) | 6.86 (6.93) | 4.29 (4.38) |
| 103 |  | H | —C₂H₅ |  | Cl | 70.21 (70.31) | 5.86 (5.90) | 3.50 (3.42) |
| 104 |  | H | —C₃H₇ | —CH₂OCH₃ | Cl | 64.08 (63.94) | 7.20 (7.15) | 4.79 (4.97) |
| 105 |  | H | —C₃H₇ | —(CH₂)₂OC₂H₅ | Cl | 64.21 (64.09) | 8.69 (8.74) | 4.58 (4.67) |

TABLE 2-continued
| No. | R₁ | R₂ | R₃ | R₄ | Y | Elemental analysis values (%) (calculated values in the parentheses) | | | | | |
|---|---|---|---|---|---|---|---|---|---|---|---|
| | | | | | | C | | H | | N | |
| 106 |  | H | —C₄H₉ | —CH₂CH₂OCH₃ | Cl | 65.63 | (65.90) | 7.88 | (7.81) | 4.55 | (4.52) |
| 107 |  | H | —C₄H₉ |  | Cl | 73.38 | (73.27) | 6.85 | (6.76) | 4.20 | (4.27) |
| 108 |  | H | —C₄H₉ |  CH₃ / C₂H₅ | Cl | 74.79 | (74.68) | 7.58 | (7.63) | 3.77 | (3.79) |
| 109 |  | H | —C₄H₉ | —CH₂C≡CH | Cl | 70.74 | (70.46) | 6.88 | (6.96) | 4.79 | (4.83) |
| 110 |  | H | —C₅H₁₁ | —CH₃ | Cl | 68.60 | (68.68) | 7.96 | (7.92) | 5.11 | (5.01) |
| 111 |  | H | —C₆H₁₃ | —CH₂CH₂CN | Cl | 68.66 | (68.56) | 7.48 | (7.57) | 8.41 | (8.42) |
| 112 |  | —CH₃ | —CH₃ | —C₂H₅ | Cl | 66.56 | (66.79) | 7.23 | (7.21) | 5.59 | (5.56) |
| 113 |  | —CH₃ | —CH₃ | —CH₂CH₂CH₃ | Cl | 67.50 | (67.79) | 7.57 | (7.58) | 5.14 | (5.27) |

TABLE 2-continued

| No. | R₁ | R₂ | R₃ | R₄ | Y | Elemental analysis values (%) (calculated values in the parentheses) | | | | | |
|---|---|---|---|---|---|---|---|---|---|---|---|
| 114 | phenyl | —CH₃ | —CH₃ | —CH(CH₃)CH₃ | Cl | C | 67.60 (67.79) | H | 7.48 (7.58) | N | 5.12 (5.27) |
| 115 | phenyl | —CH₃ | —CH₃ | —CH(CH₃)CHC₂H₅ | Cl | C | 68.54 (68.68) | H | 7.88 (7.92) | N | 5.08 (5.01) |
| 116 | phenyl | —CH₃ | —CH₃ | —CH₂CH(CH₃)CH₃ | Cl | C | 68.42 (68.68) | H | 7.94 (7.92) | N | 5.12 (5.01) |
| 117 | phenyl | —CH₃ | —CH₃ | ─(CH₂)₅CH₃ | Cl | C | 69.97 (70.23) | H | 8.56 (8.51) | N | 4.80 (4.55) |
| 118 | 3,4-dimethylphenyl | —CH₃ | —CH₃ | —CH₂CH₂Cl | Cl | C | 60.84 (61.15) | H | 6.91 (6.74) | N | 4.53 (4.46) |
| 119 | phenyl | —CH₃ | —CH₃ | —CH₂CH₂CF₃ | Cl | C | 56.19 (56.34) | H | 5.35 (5.36) | N | 4.43 (4.38) |
| 120 | 3-chloro-5-methylfuryl | —CH₃ | —CH₃ | ─(CH₂)₅Br | Cl | C | 45.47 (45.37) | H | 5.06 (5.08) | N | 3.40 (3.53) |
| 121 | 2,3-dimethylphenyl | —CH₃ | —CH₃ | —CH₂OC₂H₅ | Cl | C | 64.82 (64.97) | H | 7.56 (7.50) | N | 5.00 (4.74) |

TABLE 2-continued

| No. | R₁ | R₂ | R₃ | R₄ | Y | Elemental analysis values (%) (calculated values in the parentheses) | | |
|---|---|---|---|---|---|---|---|---|
| 122 | 3-methylphenyl | —CH₃ | —CH₃ | —CH₂OC₂H₅ | Cl | C 64.71 (64.97) | H 7.72 (7.50) | N 4.76 (4.74) |
| 123 | 2-chlorophenyl | —CH₃ | —CH₃ | —CH₂OC₂H₅ | Cl | C 56.75 (56.97) | H 5.88 (6.06) | N 4.52 (4.43) |
| 124 | 2-methoxyphenyl | —CH₃ | —CH₃ | —CH₂OC₂H₅ | Cl | C 61.90 (61.63) | H 7.24 (7.11) | N 4.50 (4.49) |
| 125 | 1-naphthyl | —CH₃ | —CH₃ | —CH₂OC₂H₅ | Cl | C 69.05 (68.77) | H 6.56 (6.68) | N 4.40 (4.22) |
| 126 | 2-naphthyl | —CH₃ | —CH₃ | —CH₂OC₂H₅ | Cl | C 68.92 (68.77) | H 6.71 (6.68) | N 4.33 (4.22) |
| 127 | 2-chlorothienyl | —CH₃ | —CH₃ | —CH₂OC₂H₅ | Cl | C 48.43 (48.45) | H 5.39 (5.32) | N 3.97 (3.98) |
| 128 | phenyl | —CH₃ | —CH₃ | —CH₂OC₃H₇ | Cl | C 65.20 (64.97) | H 7.48 (7.50) | N 4.67 (4.74) |

TABLE 2-continued

| No. | R₁ | R₂ | R₃ | R₄ | Y | Elemental analysis values (%) (calculated values in the parentheses) | | |
|---|---|---|---|---|---|---|---|---|
| 129 | 5-methylthio-furan-2-yl (CH₃S-furan-CH₃) | —CH₃ | —CH₃ | —CH₂OC₄H₉ | Cl | C 55.50 (55.56) | H 7.08 (6.99) | N 3.94 (4.05) |
| 130 | 2-methylphenyl | —CH₃ | —CH₃ | —CH₂CH₂OCH₃ | Cl | C 64.79 (64.97) | H 7.71 (7.50) | N 4.82 (4.74) |
| 131 | 4-methylphenyl | —CH₃ | —CH₃ | —CH₂CH₂OCH₃ | Cl | C 64.70 (64.97) | H 7.72 (7.50) | N 4.69 (4.74) |
| 132 | 4-methyl-α,α-dimethylbenzyl | —CH₃ | —CH₃ | —CH₂CH₂OCH₃ | Cl | C 67.27 (67.54) | H 8.40 (8.35) | N 4.17 (4.15) |
| 133 | 2-chlorophenyl | —CH₃ | —CH₃ | —CH₂CH₂OCH₃ | Cl | C 56.99 (56.97) | H 5.99 (6.06) | N 4.54 (4.43) |
| 134 | 3-chlorophenyl | —CH₃ | —CH₃ | —CH₂CH₂OCH₃ | Cl | C 56.77 (56.97) | H 6.10 (6.06) | N 4.47 (4.43) |
| 135 | 4-bromophenyl | —CH₃ | —CH₃ | —CH₂CH₂OCH₃ | Cl | C 49.97 (49.95) | H 5.34 (5.31) | N 3.87 (3.88) |

TABLE 2-continued
| No. | R₁ | R₂ | R₃ | R₄ | Y | Elemental analysis values (%) (calculated values in the parentheses) | | |
|---|---|---|---|---|---|---|---|---|
| | | | | | | C | H | N |
| 136 | 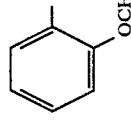 | —CH₃ | —CH₃ | —CH₂CH₂OCH₃ | Cl | 61.82 (61.63) | 7.17 (7.11) | 4.64 (4.49) |
| 137 |  | —CH₃ | —CH₃ | —CH₂CH₂OCH₃ | Cl | 61.54 (61.63) | 7.22 (7.11) | 4.37 (4.49) |
| 138 | 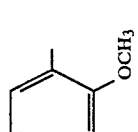 | —CH₃ | —CH₃ | —CH₂CH₂OCH₃ | Cl | 58.43 (58.61) | 6.80 (6.76) | 4.30 (4.27) |
| 139 |  | —CH₃ | —CH₃ | —CH₂CH₂OCH₃ | Cl | 67.41 (67.46) | 6.45 (6.47) | 3.71 (3.75) |
| 140 |  | —CH₃ | —CH₃ | —CH₂CH₂OCH₃ | Cl | 67.18 (67.46) | 6.24 (6.47) | 3.81 (3.75) |
| 141 |  | —CH₃ | —CH₃ | —CH₂CH₂OCH₃ | Cl | 66.15 (65.90) | 7.86 (7.81) | 4.55 (4.52) |

TABLE 2-continued

| No. | R₁ | R₂ | R₃ | R₄ | Y | Elemental analysis values (%) (calculated values in the parentheses) | | |
|---|---|---|---|---|---|---|---|---|
| 142 | 2,4-dimethylphenyl | —CH₃ | —CH₃ | —CH₂CH₂OCH₃ | Cl | C 65.93 (65.90) | H 7.82 (7.81) | N 4.47 (4.52) |
| 143 | 4-isopropyl-3-methylphenyl | —CH₃ | —CH₃ | —CH₂CH₂OCH₃ | Cl | C 67.28 (67.54) | H 8.39 (8.35) | N 4.28 (4.15) |
| 144 | 8-methylnaphthyl | —CH₃ | —CH₃ | —CH₂CH₂OCH₃ | Cl | C 68.53 (68.77) | H 6.59 (6.68) | N 4.46 (4.22) |
| 145 | 2-methylfuryl | —CH₃ | —CH₃ | —CH₂CH₂OCH₃ | Cl | C 57.21 (57.46) | H 6.71 (6.68) | N 5.32 (5.15) |
| 146 | 5-methyl-2-furyl | —CH₃ | —CH₃ | —CH₂CH₂OCH₃ | Cl | C 58.61 (58.84) | H 7.03 (7.05) | N 4.99 (4.90) |
| 147 | 2-bromo-5-methylthienyl | —CH₃ | —CH₃ | —CH₂CH₂OCH₃ | Cl | C 42.69 (42.58) | H 4.70 (4.67) | N 3.83 (3.82) |
| 148 | phenyl | —CH₃ | —CH₃ | CH₃—CHOCH₃ | Cl | C 64.16 (63.94) | H 6.97 (7.15) | N 5.22 (4.97) |

TABLE 2-continued
| No. | R₁ | R₂ | R₃ | R₄ | Y | Elemental analysis values (%) (calculated values in the parentheses) | | |
|---|---|---|---|---|---|---|---|---|
| 149 |  | —CH₃ | —CH₃ | —CH₂CH₂OC₂H₅ | Cl | C 68.13 (68.26) | H 8.74 (8.59) | N 3.96 (3.98) |
| 150 |  | —CH₃ | —CH₃ | —CH₂CH₂OC₃H₇ | Cl | C 59.94 (60.10) | H 7.38 (7.40) | N 4.65 (4.67) |
| 151 |  | —CH₃ | —CH₃ | —CH₂CH₂OC₅H₁₁ | Cl | C 67.29 (67.54) | H 8.34 (8.35) | N 4.43 (4.15) |
| 152 | 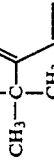 | —CH₃ | —CH₃ | —CH₂CH(OCH₃)(OCH₃) | Cl | C 61.45 (61.63) | H 7.16 (7.11) | N 4.49 (4.49) |
| 153 |  | —CH₃ | —CH₃ | —CH₂CH(OC₂H₅)(OC₂H₅) | Cl | C 63.39 (63.61) | H 7.80 (7.71) | N 4.18 (4.12) |
| 154 |  | —CH₃ | —CH₃ | (CH₂)₃OCH₃ | Cl | C 65.03 (64.97) | H 7.49 (7.50) | N 4.86 (4.74) |
| 155 |  | —CH₃ | —CH₃ | (CH₂)₃OCH₃ | Cl | C 65.65 (65.90) | H 8.01 (7.81) | N 4.55 (4.52) |
| 156 |  | —CH₃ | —CH₃ | (CH₂)₃OC₂H₅ | Cl | C 65.80 (65.90) | H 7.79 (7.81) | N 4.60 (4.52) |

TABLE 2-continued

| No. | R₁ | R₂ | R₃ | R₄ | Y | Elemental analysis values (%) (calculated values in the parentheses) | | | | | |
|---|---|---|---|---|---|---|---|---|---|---|---|
| | | | | | | | C | | H | | N |
| 157 | phenyl | —CH₃ | —CH₃ | ⁺CH₂₎₃OCH(CH₃)CH₃ | Cl | C | 66.61 (66.76) | H | 8.17 (8.09) | N | 4.42 (4.32) |
| 158 | phenyl | —CH₃ | —CH₃ | ⁺CH₂₎₄OCH₃ | Cl | C | 65.65 (65.90) | H | 7.84 (7.81) | N | 4.58 (4.52) |
| 159 | phenyl | —CH₃ | —CH₃ | —CH(C₂H₅)CH₂OCH₃ | Cl | C | 65.90 (65.90) | H | 7.76 (7.81) | N | 4.56 (4.52) |
| 160 | phenyl | —CH₃ | —CH₃ | —CH₂CH₂SC₃H₇ | Cl | C | 62.64 (62.65) | H | 7.58 (7.42) | N | 4.27 (4.30) |
| 161 | phenyl | —CH₃ | —CH₃ | ⁺CH₂₎₃SCH₃ | Cl | C | 61.43 (61.62) | H | 7.14 (7.11) | N | 4.50 (4.49) |
| 162 | phenyl | —CH₃ | —CH₃ | —CH₂CH₂—O—(4-Cl-C₆H₄) | Cl | C | 63.72 (63.50) | H | 5.53 (5.60) | N | 3.65 (3.70) |
| 163 | phenyl | —CH₃ | —CH₃ | —CH₂CH₂CN | Cl | C | 65.30 (65.10) | H | 5.99 (6.19) | N | 9.90 (10.12) |
| 164 | phenyl | —CH₃ | —CH₃ | —CH₂—C₆H₅ | Cl | C | 72.62 (72.72) | H | 6.44 (6.42) | N | 4.48 (4.46) |

TABLE 2-continued
| No. | R₁ | R₂ | R₃ | R₄ | Y | Elemental analysis values (%) (calculated values in the parentheses) | | |
|---|---|---|---|---|---|---|---|---|
| 165 | 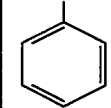 | —CH₃ | —CH₃ |  | Cl | C 70.10 (69.86) | H 6.52 (6.45) | N 4.10 (4.07) |
| 166 |  | —CH₃ | —CH₃ |  | Cl | C 66.18 (66.33) | H 7.16 (7.20) | N 4.71 (4.55) |
| 167 | 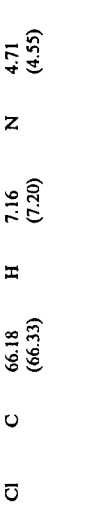 | —CH₃ | —CH₃ | 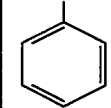 | Cl | C 63.48 (63.26) | H 5.91 (5.97) | N 13.80 (13.83) |
| 168 |  | —CH₃ | —CH₃ | 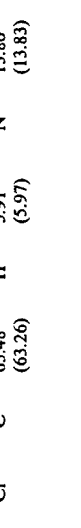 | Cl | C 63.47 (63.65) | H 6.48 (6.60) | N 8.92 (8.73) |
| 169 | 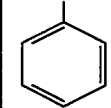 | —CH₃ | —CH₃ |  | Cl | C 66.21 (66.33) | H 7.16 (7.20) | N 4.70 (4.55) |
| 170 | 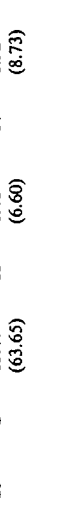 | —CH₃ | —CH₃ | 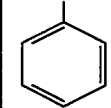 | Cl | C 69.49 (69.68) | H 8.25 (8.36) | N 7.80 (7.74) |
| 171 |  | —CH₃ | —CH₃ | —CH₂COOC₂H₅ | Cl | C 62.09 (62.03) | H 6.50 (6.51) | N 4.62 (4.52) |
| 172 | 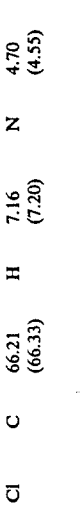 | —CH₃ | —CH₃ | CH₃<br>\|<br>—CHCOOCH₃ | Cl | C 62.19 (62.03) | H 6.55 (6.51) | N 4.61 (4.52) |

TABLE 2-continued

| No. | R$_1$ | R$_2$ | R$_3$ | R$_4$ | Y | Elemental analysis values (%) (calculated values in the parentheses) | | |
|---|---|---|---|---|---|---|---|---|
| | | | | | | C | H | N |
| 173 | phenyl | —CH$_3$ | —CH$_3$ | —CH(CH$_3$)COOC$_2$H$_5$ | Cl | 62.81 (63.06) | 6.77 (6.85) | 4.55 (4.33) |
| 174 | 2-methylphenyl | —CH$_3$ | —CH$_3$ | —(CH$_2$)$_3$COOC$_2$H$_5$ | Cl | 64.89 (64.86) | 7.39 (7.45) | 4.12 (3.98) |
| 175 | phenyl | —CH$_3$ | —CH$_3$ | —CH(CH$_3$)CH$_2$OCH$_2$CH=CH$_2$ | Cl | 66.90 (67.17) | 7.70 (7.52) | 4.35 (4.35) |
| 176 | phenyl | —CH$_3$ | —CH$_3$ | —CH$_2$CH$_2$OCH$_2$C≡CH | Cl | 66.90 (66.77) | 6.54 (6.59) | 4.55 (4.58) |
| 177 | phenyl | —CH$_3$ | —CH$_3$ | —CH$_2$CH$_2$OCCH$_3$ (O=) | Cl | 62.21 (62.03) | 6.48 (6.51) | 4.49 (4.52) |
| 178 | phenyl | —CH$_3$ | —CH$_3$ | phenyl (4-methyl) | Cl | 71.88 (72.11) | 5.92 (6.05) | 4.63 (4.67) |
| 179 | phenyl | —CH$_3$ | —CH$_3$ | 4-chlorophenyl | Cl | 64.41 (64.68) | 5.13 (5.13) | 4.01 (4.19) |

TABLE 2-continued
| No. | R₁ | R₂ | R₃ | R₄ | Y | Elemental analysis values (%) (calculated values in the parentheses) | | |
|---|---|---|---|---|---|---|---|---|
| 180 | 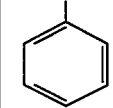 | —CH₃ | —CH₃ | 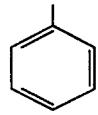 | Cl | C 73.30 (73.27) | H 6.76 (6.76) | N 4.39 (4.27) |
| 181 | 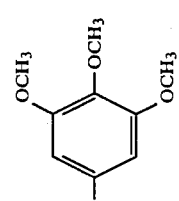 | —CH₃ | —CH₃ | 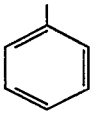 | Cl | C 64.85 (64.69) | H 6.14 (6.20) | N 3.56 (3.59) |
| 182 | 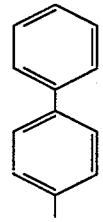 | —CH₃ | —CH₃ | 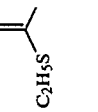 | Cl | C 76.72 (76.69) | H 5.76 (5.90) | N 3.79 (3.73) |
| 183 | 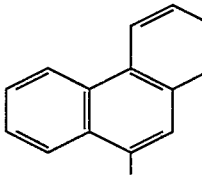 | —CH₃ | —CH₃ | 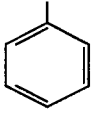 | Cl | C 67.25 (67.01) | H 5.08 (5.19) | N 3.00 (3.01) |
| 184 | 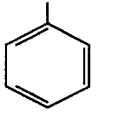 | —CH₃ | —CH₃ | —CH=CH₂ | Cl | C 67.08 (67.33) | H 6.51 (6.46) | N 5.63 (5.61) |
| 185 |  | —CH₃ | —CH₃ | $\begin{array}{c}CH_3\\ |\\ -C=CH_2\end{array}$ | Cl | C 68.22 (68.30) | H 6.86 (6.88) | N 5.34 (5.31) |

TABLE 2-continued

| No. | R₁ | R₂ | R₃ | R₄ | Y | Elemental analysis values (%) (calculated values in the parentheses) | | | | | |
|---|---|---|---|---|---|---|---|---|---|---|---|
| | | | | | | C | | H | | N | |
| 186 | phenyl | —CH₃ | —CH₃ | —CH=C(CH₃)(CH₃) | Cl | C | 69.04 (69.18) | H | 7.30 (7.26) | N | 5.06 (5.04) |
| 187 | phenyl | —CH₃ | —CH₃ | —CH₂CH₂CH=CH₂ | Cl | C | 69.41 (69.18) | H | 7.22 (7.26) | N | 4.98 (5.04) |
| 188 | 4-CF₃-phenyl | —CH₃ | —CH₃ | —CH₂CH₂C≡CH | Cl | C | 59.44 (59.40) | H | 5.01 (4.98) | N | 3.96 (4.07) |
| 189 | phenyl | —CH₃ | —C₂H₅ | —CH₃ | Cl | C | 66.52 (66.79) | H | 7.28 (7.21) | N | 5.61 (5.56) |
| 190 | 4-F-phenyl | —CH₃ | —C₂H₅ | —CH₃ | Cl | C | 62.49 (62.34) | H | 6.34 (6.35) | N | 5.12 (5.19) |
| 191 | phenyl | —CH₃ | —C₂H₅ | —CH₂CH₂OC₂H₅ | Cl | C | 65.64 (65.90) | H | 7.73 (7.81) | N | 4.58 (4.52) |
| 192 | 2-Cl-4-(4-methylphenoxy)phenyl | —CH₃ | —C₂H₅ | ―(CH₂)₃OC₃H₇ | Cl | C | 64.72 (64.65) | H | 6.71 (6.73) | N | 3.00 (3.02) |
| 193 | phenyl | —CH₃ | —C₂H₅ | —CH₂CH₂O-(4-methylphenyl) | Cl | C | 71.12 (71.05) | H | 6.99 (7.05) | N | 3.74 (3.77) |

TABLE 2-continued
| No. | $R_1$ | $R_2$ | $R_3$ | $R_4$ | Y | Elemental analysis values (%) (calculated values in the parentheses) | | |
|---|---|---|---|---|---|---|---|---|
| 194 | 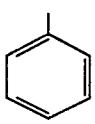 | —CH₃ | —C₂H₅ | —CH₂CH₂COOCH₃ | Cl | C 63.25 (63.06) | H 6.93 (6.85) | N 4.15 (4.33) |
| 195 |  | —CH₃ | —C₂H₅ | —CH₂CH₂OCH₂CH=CH₂ | Cl | C 67.30 (67.17) | H 7.50 (7.52) | N 4.31 (4.35) |
| 196 |  | —CH₃ | —C₂H₅ | —CH₂CH₂OCH₂CH=CH₂ | Cl | C 59.94 (59.73) | H 7.02 (7.08) | N 4.05 (4.10) |
| 197 |  | —CH₃ | —C₂H₅ | —CH=CH₂ | Cl | C 68.12 (68.30) | H 6.91 (6.88) | N 5.34 (5.31) |
| 198 |  | —CH₃ | —C₃H₇ | —CH₂CH₂OCH₃ | Cl | C 65.66 (65.90) | H 7.75 (7.81) | N 4.59 (4.52) |
| 199 |  | —CH₃ | —C₃H₇ | —CH₂CH=CH₂ | Cl | C 68.92 (68.66) | H 6.23 (6.26) | N 3.44 (3.48) |
| 200 |  | —CH₃ | —C₄H₉ | —CH₂OCH₃ | Cl | C 57.04 (57.22) | H 6.18 (6.14) | N 3.75 (3.71) |
| 201 |  | —C₂H₅ | —C₂H₅ |  | Cl | C 69.70 (69.49) | H 8.12 (8.23) | N 4.73 (4.77) |

TABLE 2-continued

| No. | R$_1$ | R$_2$ | R$_3$ | R$_4$ | Y | Elemental analysis values (%) (calculated values in the parentheses) | | |
|---|---|---|---|---|---|---|---|---|
| | | | | | | C | H | N |
| 202 | 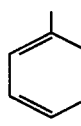 | —C$_2$H$_5$ | —C$_2$H$_5$ | —CH$_2$OC$_2$H$_5$ | Cl | 65.75 (65.90) | 7.82 (7.81) | 4.49 (4.52) |
| 203 |  | —C$_2$H$_5$ | —C$_2$H$_5$ | —CH$_2$CH$_2$OCH$_3$ | Cl | 65.76 (65.90) | 7.84 (7.81) | 4.62 (4.52) |
| 204 | 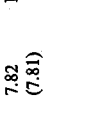 | —C$_2$H$_5$ | —C$_2$H$_5$ | —CH$_2$COOCH$_3$ | Cl | 63.14 (63.06) | 6.78 (6.85) | 4.27 (4.33) |
| 205 |  | —C$_2$H$_5$ | —C$_2$H$_5$ | —CH$_2$CH$_2$OCC$_2$H$_5$ (O=) | Cl | 57.42 (57.21) | 5.93 (6.00) | 3.35 (3.34) |
| 206 |  | —C$_2$H$_5$ | —C$_2$H$_5$ | —CH(CH$_3$)–phenyl(CH$_3$) | Cl | 74.72 (74.68) | 7.57 (7.63) | 3.83 (3.79) |
| 207 | 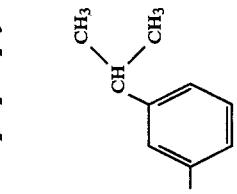 | —C$_2$H$_5$ | —C$_2$H$_5$ | —CH$_2$CH=CH$_2$ | Cl | 49.12 (48.88) | 5.04 (5.07) | 3.28 (3.35) |
| 208 |  | —C$_2$H$_5$ | —C$_3$H$_7$ | —CH$_2$CH$_2$OC$_2$H$_5$ | Cl | 67.71 (67.54) | 8.41 (8.35) | 4.07 (4.15) |
| 209 | 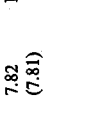 | —C$_2$H$_5$ | —C$_3$H$_7$ | —CH$_2$CH$_2$OC$_3$H$_7$ | Cl | 68.42 (68.26) | 8.54 (8.59) | 3.95 (3.98) |

TABLE 2-continued

| No. | R₁ | R₂ | R₃ | R₄ | Y | Elemental analysis values (%) (calculated values in the parentheses) | | |
|---|---|---|---|---|---|---|---|---|
| 210 | phenyl | —C₃H₇ | —C₃H₇ | —CH₃ | Cl | C 69.78 (69.49) | H 8.29 (8.23) | N 4.70 (4.77) |
| 211 | phenyl | —C₃H₇ | —C₃H₇ | —(CH₂)₃OCH₃ | Cl | C 67.83 (67.68) | H 9.51 (9.37) | N 3.87 (3.95) |
| 212 | phenyl | —C₄H₉ | —C₄H₉ | —C₂H₅ | Cl | C 71.64 (71.51) | H 8.92 (9.00) | N 4.09 (4.17) |
| 213 | phenyl | H | —OCH₃ | —C₃H₇ | Cl | C 63.04 (62.80) | H 6.73 (6.78) | N 5.20 (5.23) |
| 214 | 3-ClCH₂-phenyl | H | —OCH₃ | —C₄H₉ | Cl | C 58.01 (58.19) | H 6.45 (6.41) | N 4.27 (4.24) |
| 215 | phenyl | H | —OCH₃ | —CH₂CH₂OCH₃ | Cl | C 59.08 (59.26) | H 6.43 (6.39) | N 4.95 (4.94) |
| 216 | phenyl | H | —OCH₃ | —CH₂CH₂-(2-thienyl) | Cl | C 61.32 (61.16) | H 4.80 (4.83) | N 4.17 (4.20) |
| 217 | phenyl | H | —OCH₃ | phenyl | Cl | C 68.29 (68.12) | H 4.65 (4.71) | N 4.60 (4.67) |

TABLE 2-continued
| No. | R₁ | R₂ | R₃ | R₄ | Y | Elemental analysis values (%) (calculated values in the parentheses) | | |
|---|---|---|---|---|---|---|---|---|
| | | | | | | C | H | N |
| 218 | 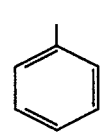 | H | —OCH₃ | 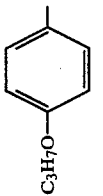 2,6-(CH₃)₂ | Cl | 68.93 (69.19) | 6.18 (6.11) | 4.29 (4.25) |
| 219 | C₃H₇O—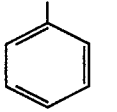 | H | —OCH₃ | 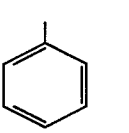 2,6-(CH₃)₂ | Cl | 68.30 (68.12) | 6.74 (6.76) | 3.52 (3.61) |
| 220 | 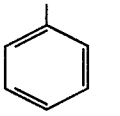 | H | —OCH₃ | 2-CH₃, 6-C₂H₅ phenyl | Cl | 69.96 (69.86) | 6.40 (6.45) | 4.11 (4.07) |
| 221 | phenyl | H | —OCH₃ | 2,3-Cl₂ phenyl | Cl | 54.92 (55.09) | 3.77 (3.81) | 3.82 (3.78) |
| 222 | phenyl | H | —OCH₃ | —CH₂CH=CH₂ | Cl | 63.17 (63.28) | 6.21 (6.07) | 5.38 (5.27) |
| 223 |  2-OC₂H₅ | H | —OC₂H₅ | —CH₂OC₄H₉ | Cl | 61.93 (61.70) | 7.58 (7.63) | 3.75 (3.79) |

TABLE 2-continued
| No. | R₁ | R₂ | R₃ | R₄ | Y | Elemental analysis values (%) (calculated values in the parentheses) | | |
|---|---|---|---|---|---|---|---|---|
| | | | | | | C | H | N |
| 224 |  | H | —OC₃H₇ | —CH₂CH₂OCH₃ | Cl | 61.49 (61.63) | 7.05 (7.11) | 4.44 (4.49) |
| 225 |  | —CH₃ | —OCH₃ | —CH₂OC₃H₇ | Cl | 62.15 (62.03) | 6.48 (6.51) | 4.49 (4.52) |
| 226 |  | —CH₃ | —OCH₃ | —CH₂CH₂OCH₃ | Cl | 62.83 (62.67) | 7.40 (7.42) | 4.31 (4.30) |
| 227 |  | —CH₃ | —OCH₃ | —CH₂CH₂OC₂H₅ | Cl | 61.79 (61.63) | 7.00 (7.11) | 4.45 (4.49) |
| 228 |  | —CH₃ | —OCH₃ | —CH₂COOC₄H₉ | Cl | 61.28 (61.10) | 6.82 (6.84) | 3.91 (3.96) |
| 229 |  | —CH₃ | —OCH₃ |  | Cl | 66.22 (65.99) | 5.80 (5.83) | 3.98 (4.05) |
| 230 |  | —CH₃ | —OCH₃ | —CH=CH₂ | Cl | 61.07 (61.24) | 4.93 (4.88) | 3.61 (3.57) |

TABLE 2-continued

| No. | R$_1$ | R$_2$ | R$_3$ | R$_4$ | Y | Elemental analysis values (%) (calculated values in the parentheses) | | |
|---|---|---|---|---|---|---|---|---|
| | | | | | | C | H | N |
| 231 | C$_4$H$_9$O-C$_6$H$_4$- | —CH$_3$ | —OC$_5$H$_{11}$ | —C$_2$H$_5$ | Cl | 66.49 (66.73) | 8.61 (8.65) | 3.62 (3.54) |
| 232 | C$_6$H$_5$- | —C$_2$H$_5$ | —OCH$_3$ | —(CH$_2$)$_4$CH$_3$ | Cl | 66.94 (66.76) | 8.05 (8.09) | 4.27 (4.32) |
| 233 | 2-methyl-5-CH$_3$-thienyl | —C$_2$H$_5$ | —OCH$_3$ | —CH$_2$CH$_2$OC$_2$H$_5$ | Cl | 55.71 (55.56) | 6.92 (6.99) | 4.00 (4.05) |
| 234 | C$_6$H$_5$- | —C$_3$H$_7$ | —OCH$_3$ | —CH≡CH | Cl | 66.88 (66.77) | 6.58 (6.59) | 4.52 (4.58) |
| 235 | 4-CH$_3$-C$_6$H$_4$- | —C$_5$H$_{11}$ | —OC$_2$H$_5$ | —C$_5$H$_{11}$ | Cl | 64.03 (63.76) | 8.01 (8.03) | 3.35 (3.38) |
| 236 | 4-Cl-C$_6$H$_4$- | —OCH$_3$ | —OCH$_3$ | —CH$_2$CH$_2$OC$_3$H$_7$ | Cl | 40.91 (40.79) | 4.77 (4.79) | 3.11 (3.17) |
| 237 | 2-methyl-5-I-furyl | —OCH$_3$ | —OCH$_3$ | —(CH$_2$)$_3$OCH$_3$ | Cl | 58.74 (58.62) | 6.75 (6.76) | 4.22 (4.27) |
| 238 | C$_6$H$_5$- | —OCH$_3$ | —OCH$_3$ | —C$_6$H$_5$ | Cl | 65.29 (65.16) | 5.42 (5.47) | 4.16 (4.22) |
| 239 | C$_6$H$_5$- | —OC$_2$H$_5$ | —OC$_2$H$_5$ | —CH$_2$CH$_2$SC$_2$H$_5$ | Cl | 58.00 (58.13) | 7.12 (7.05) | 3.93 (3.77) |

TABLE 2-continued
| No. | R$_1$ | R$_2$ | R$_3$ | R$_4$ | Y | Elemental analysis values (%) (calculated values in the parentheses) | | |
|---|---|---|---|---|---|---|---|---|
| | | | | | | C | H | N |
| 240 | 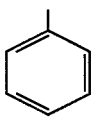 | —OC$_2$H$_5$ | —OC$_3$H$_7$ | —CH$_2$CH$_2$CN | Cl | 61.47 (61.62) | 6.58 (6.61) | 8.00 (7.98) |
| 241 |  | CH$_2$—CH$_2$ | | —CH$_2$CH$_2$CH$_3$ | Cl | 68.48 (68.30) | 6.82 (6.88) | 5.29 (5.31) |
| 242 |  | CH$_2$—CH$_2$ | |  (2,6-diethylphenyl) | Cl | 62.84 (63.04) | 6.01 (5.97) | 3.42 (3.61) |
| 243 |  | CH$_2$—CH$_2$—CH$_2$ | | —CH$_2$OCH(CH$_3$)$_2$ | Cl | 67.30 (67.17) | 7.50 (7.52) | 4.27 (4.35) |
| 244 |  | CH$_2$—CH$_2$—CH$_2$ | | —CH$_2$CH$_2$O-(3-propoxyphenyl) | Cl | 69.41 (69.64) | 6.89 (6.82) | 3.43 (3.38) |
| 245 | 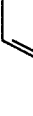 | CH$_2$—CH$_2$—CH$_2$ | | —CH(CH$_3$)—N(pyrrole) | Cl | 60.45 (60.53) | 5.01 (5.08) | 7.12 (7.06) |
| 246 |  | CH$_2$—CH$_2$—CH$_2$—CH$_2$ | | —(CH$_2$)$_3$-(4-chlorophenyl) | Cl | 68.90 (68.66) | 6.41 (6.26) | 3.32 (3.48) |

TABLE 2-continued

| No. | R₁ | R₂ | R₃ | R₄ | Y | Elemental analysis values (%) (calculated values in the parentheses) | | | | | |
|---|---|---|---|---|---|---|---|---|---|---|---|
| 247 | naphthyl | | $-CH_2-CH_2-CH_2-CH_2-CH_2-$ (piperidyl) | $-CH_2C\equiv CH$ | Cl | C | 74.85 (74.66) | H | 6.00 (5.97) | N | 4.08 (4.15) |
| 248 | phenyl | | $-CH_2-CH_2-O-CH_2-CH_2-$ (morpholinyl) | $-CH_2CH_2OCH_3$ | Cl | C | 67.03 (67.17) | H | 7.47 (7.52) | N | 4.42 (4.35) |
| 249 | 3-Cl-phenyl | | $-CH_2-CH_2-O-CH_2-CH_2-$ (morpholinyl) | $-CH_2CH_2OCH_3$ | Cl | C | 60.79 (60.68) | H | 6.48 (6.51) | N | 3.84 (3.93) |
| 250 | phenyl | | $-CH_2-CH_2-O-CH_2-CH_2-$ (morpholinyl) | $-CH_2CH_2OC_2H_5$ | Cl | C | 67.95 (67.95) | H | 7.58 (7.80) | N | 4.30 (4.17) |
| 251 | phenyl | H | H | $-CH_2CH_2O-C_6H_4-Br$ | Br | C | 49.41 (49.23) | H | 3.85 (3.90) | N | 3.12 (3.19) |
| 252 | phenyl | H | H | $-(CH_2)_7COOC_4H_9$ | Br | C | 56.30 (56.55) | H | 6.29 (6.33) | N | 3.74 (3.66) |

TABLE 2-continued
| No. | R₁ | R₂ | R₃ | R₄ | Y | Elemental analysis values (%) (calculated values in the parentheses) | | |
|---|---|---|---|---|---|---|---|---|
| | | | | | | C | H | N |
| 253 |  | H | H | 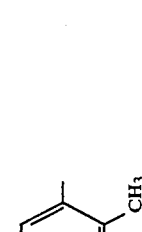 | Br | 62.67 (62.80) | 5.33 (5.27) | 4.00 (4.07) |
| 254 | 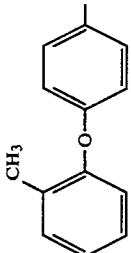 | H | H |  | Br | 63.95 (63.70) | 5.49 (5.36) | 3.88 (3.91) |
| 255 |  | H | —CH₃ | —CH₃ | Br | 56.01 (55.83) | 4.63 (4.69) | 3.37 (3.43) |
| 256 |  | H | —CH₃ | —CH₂OC₄H₉ | Br | 56.24 (56.48) | 6.59 (6.52) | 4.12 (4.12) |
| 257 |  | H | —CH₃ | —CH₂O—⌬—SCH₃ | Br | 55.92 (56.16) | 4.91 (4.96) | 3.38 (3.45) |
| 258 |  | H | —CH₃ | —CH₂CH₂—⌬—C₃H₇ | Br | 66.20 (66.00) | 6.47 (6.55) | 3.45 (3.50) |
| 259 |  | H | —CH₃ | —CH₂CH₂O⟨O⟩CH₃ | Br | 59.34 (59.19) | 6.40 (6.35) | 3.76 (3.83) |

TABLE 2-continued

| No. | R₁ | R₂ | R₃ | R₄ | Y | Elemental analysis values (%) (calculated values in the parentheses) | | |
|-----|----|----|----|----|----|---|---|---|
| | | | | | | C | H | N |
| 260 | 2-thienyl | H | —CH₃ | 2-ethyl-4-chlorophenyl | Br | 51.45 (51.21) | 4.21 (4.30) | 3.44 (3.51) |
| 261 | phenyl | —CH₃ | —CH₃ | —CH₃ | Br | 55.27 (55.33) | 5.77 (5.71) | 4.95 (4.96) |
| 262 | phenyl | —CH₃ | —CH₃ | —CH₂CH₂OCH₃ | Br | 55.18 (55.23) | 6.23 (6.18) | 4.28 (4.29) |
| 263 | 3-methylphenyl | —CH₃ | —CH₃ | —CH₂CH₂OCH₃ | Br | 56.29 (56.48) | 6.61 (6.52) | 4.15 (4.12) |
| 264 | 4-(4-methylphenoxy)phenyl | —CH₃ | —CH₃ | —CH₂CH₂OCH₃ | Br | 60.50 (60.29) | 5.72 (5.78) | 3.24 (3.35) |
| 265 | phenyl | —CH₃ | —CH₃ | —CH₂CH₂OC₂H₅ | Br | 56.32 (56.48) | 6.48 (6.52) | 4.23 (4.12) |
| 266 | 5-methyl-2-ethylfuryl | —CH₃ | —CH₃ | —CH₂CH₂OCH₂CH=CH₂ | Br | 55.31 (55.14) | 6.46 (6.53) | 3.71 (3.78) |
| 267 | phenyl | —CH₃ | —C₂H₅ | —CH₂CH₂OCH₃ | Br | 56.60 (56.48) | 6.49 (6.52) | 4.10 (4.12) |

TABLE 2-continued
| No. | R₁ | R₂ | R₃ | R₄ | Y | Elemental analysis values (%) (calculated values in the parentheses) | | |
|---|---|---|---|---|---|---|---|---|
| | | | | | | C | H | N |
| 268 | 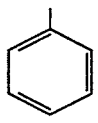 | —CH₃ | —C₂H₅ | CH₃<br>—C=CH₂ | Br | 59.79<br>(59.64) | 6.21<br>(6.26) | 4.28<br>(4.35) |
| 269 | 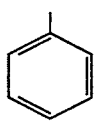 | —C₂H₅ | —C₂H₅ | —CH₂CH₃ | Br | 59.45<br>(59.27) | 6.74<br>(6.84) | 4.30<br>(4.32) |
| 270 | 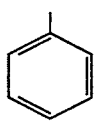 | H | —OCH₃ | 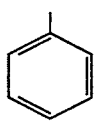 | Br | 56.92<br>(57.15) | 5.33<br>(5.27) | 3.37<br>(3.33) |
| 271 | 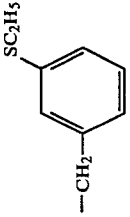 | —CH₃ | —OCH₃ | 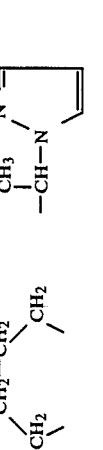 | Br | 57.30<br>(57.16) | 5.48<br>(5.33) | 3.59<br>(3.70) |
| 272 | 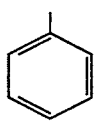 | \multicolumn{2}{c}{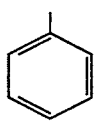} |  | Br | 59.01<br>(58.77) | 5.66<br>(5.71) | 10.78<br>(10.82) |
| 273 | 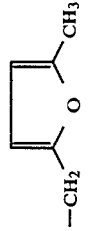 | \multicolumn{2}{c}{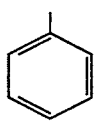} | —CH₂CH₂COOCH₃ | Br | 57.64<br>(57.88) | 6.25<br>(6.13) | 3.51<br>(3.55) |
| 274 | 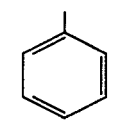 | H | H | CH₃ CH₃ (2,6-dimethylphenyl) | I | 55.09<br>(55.26) | 4.69<br>(4.64) | 3.71<br>(3.58) |

TABLE 2-continued

| No. | R₁ | R₂ | R₃ | R₄ | Y | Elemental analysis values (%) (calculated values in the parentheses) | | |
|---|---|---|---|---|---|---|---|---|
| | | | | | | C | H | N |
| 275 | 3-CH₃O-C₆H₄ | H | H | 4-Cl-2-CH₃-C₆H₃ | I | 49.08 (48.95) | 3.95 (3.88) | 3.01 (3.17) |
| 276 | C₆H₅ | H | —CH₃ | —(CH₂)₂CH(OC₂H₅)(OC₂H₅) | I | 50.27 (50.13) | 6.01 (6.08) | 3.17 (3.25) |
| 277 | C₆H₅ | H | —CH₃ | —CH₂-(tetrahydrothiophen-2-yl) | I | 48.11 (47.89) | 4.98 (5.02) | 3.43 (3.49) |
| 278 | 3-Cl-C₆H₄ | —CH₃ | —CH₃ | —CH₂CH₂OCH₃ | I | 43.95 (44.19) | 4.74 (4.70) | 3.60 (3.44) |
| 279 | C₆H₅ | —CH₃ | —CH₃ | —CH₂CH₂OC₂H₅ | I | 49.40 (49.62) | 5.79 (5.73) | 3.72 (3.62) |
| 280 | C₆H₅ | —CH₃ | —CH₃ | —CH₂CH=CH₂ | I | 50.97 (50.72) | 5.23 (5.11) | 3.86 (3.94) |
| 281 | C₆H₅ | —CH₃ | —C₂H₅ | —CH₂OC₃H₇ | I | 51.09 (50.88) | 6.08 (6.03) | 3.41 (3.49) |
| 282 | C₆H₅ | —C₂H₅ | —C₂H₅ | —CH₃ | I | 50.31 (50.43) | 5.55 (5.64) | 4.08 (3.92) |

TABLE 2-continued

| No. | R₁ | R₂ | R₃ | R₄ | Y | Elemental analysis values (%) (calculated values in the parentheses) | | |
|---|---|---|---|---|---|---|---|---|
| | | | | | | C | H | N |
| 283 | 4-I-C₆H₄- | —C₂H₅ | —C₂H₅ | ⁺(CH₂)₃OCH₃ | I | 40.19 (39.95) | 4.52 (4.66) | 2.54 (2.59) |
| 284 | C₆H₅- | H | —OCH₃ | 4-Cl-3-CH₃-C₆H₃- | I | 49.20 (48.95) | 3.84 (3.88) | 3.09 (3.17) |
| 285 | C₆H₅- | —CH₃ | —OCH₃ | —CH(CH₃)CN | I | 46.65 (46.89) | 4.40 (4.46) | 7.38 (7.29) |
| 286 | C₆H₅- | cyclopentyl | | —CH₂CH₂OCH₃ | I | 51.40 (51.14) | 5.43 (5.55) | 3.40 (3.51) |
| 287 | 3-C₄H₉-C₆H₄- | cyclohexyl | | —CH₂CH₂CH=CH₂ | I | 59.31 (59.36) | 6.90 (6.93) | 3.12 (3.01) |

FORMULATION EXAMPLE 1

Wettable powder:

Ten parts of N-(1-phenyl)ethenyl-N-chloroaceto-2',6'-dimethylanilide (compound No. 1) obtained in Example 1, 85 parts of a 2:1 mixture of Zieklite (a tradename, a product of Zieklite Kogyo K.K.) and Kunilite (tradename, a product of Kunimine Kogyo K.K.) and 5 parts of Sorpol 800A (tradename, a product of Toho Chemical Industrial Co., Ltd.) as a surfactant were mixed and pulverized uniformly to give a 10% wettable powder.

FORMULATION EXAMPLE 2

Emulsion:

Twenty parts of N-(1-phenyl-2,2-dimethyl)-ethenyl-N-chloroaceto-ethoxymethylamide (compound No. 2) obtained in Example 2, 70 parts of xylene and 10 parts of Sorpol 800A as a surfactant were mixed to form a 20% emulsion.

FORMULATION EXAMPLE 3

Granules:

Five parts of N-(1-phenyl-2,2-dimethyl)ethenyl-N-chloroaceto-2'-methoxyethylamide (compound No. 3), 50 parts of bentonite (a product of Kunimine Kogyo K.K.), 40 parts of Kunilite and 5 parts of Sorpol 800A as a surfactant were mixed and pulverized uniformly. Water was added, and the mixture was stirred uniformly to form a paste-like mixture. The mixture was extruded from a hole having a diameter of 0.7 mm, dried and cut to a length of 1 to 2 mm to form 5% granules.

EXAMPLE 7

Uplant farm soil (clay loam) was filled in porcelain pots (1/8850 ares). Seeds of various plants were sown in the soil to a depth of 0.5 to 1 cm. A water dilution of a wettable powder of each of the compounds indicated in Table 1, prepared as in Formulation Example 1, was sprayed onto the soil surface at a predetermined rate of application. After the treatment, the plants were grown in a greenhouse kept at an average atmospheric temperature of 25° C. Two weeks later, the herbicidal effect of each of the test compounds was examined, and the results are shown in Table 3.

The evaluation was made on a scale of 6 grades where 0 indicates normal growth, 5 indicates complete kill, and 1 to 4 indcate varying degrees of growth between "normal growth" and "complete kill".

A in the column of Compound No. in Table 3 is a known haloacetanilide of the following formula used for comparison.

Compound A

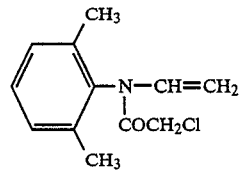

The results given in Table 3 demonstrate that the compounds of formula (I) in accordance with this invention have better herbicidal activity and selectivity than compound A.

TABLE 3

| Compound No. | Rate of application (g/10a) | a | b | c | d | e | f | g | h | i | j | k | l | m |
|---|---|---|---|---|---|---|---|---|---|---|---|---|---|---|
| 1 | 600 | 0 | 0 | 0 | 0 | 0 | 5 | 5 | 5 | 5 | 4 | 3 | 5 | 4 |
|   | 300 | 0 | 0 | 0 | 0 | 0 | 5 | 5 | 5 | 4 | 4 | 2 | 4 | 3 |
| 2 | 600 | 0 | 0 | 0 | 0 | 0 | 5 | 5 | 5 | 5 | 5 | 5 | 5 | 5 |
|   | 300 | 0 | 0 | 0 | 0 | 0 | 5 | 5 | 5 | 5 | 5 | 4 | 5 | 5 |
| 3 | 600 | 0 | 0 | 0 | 0 | 0 | 5 | 5 | 5 | 5 | 5 | 4 | 5 | 5 |
|   | 300 | 0 | 0 | 0 | 0 | 0 | 5 | 5 | 5 | 5 | 5 | 4 | 5 | 5 |
| 4 | 600 | 0 | 0 | 0 | 0 | 0 | 5 | 5 | 5 | 3 | 3 | 3 | 4 | 3 |
|   | 300 | 0 | 0 | 0 | 0 | 0 | 5 | 5 | 5 | 3 | 3 | 3 | 3 | 3 |
| 7 | 600 | 0 | 0 | 0 | 0 | 0 | 5 | 5 | 5 | 4 | 3 | 1 | 3 | 3 |
|   | 300 | 0 | 0 | 0 | 0 | 0 | 4 | 4 | 3 | 3 | 2 | 0 | 1 | 0 |
| 14 | 600 | 0 | 0 | 0 | 0 | 0 | 5 | 5 | 5 | 5 | 5 | 4 | 5 | 5 |
|   | 300 | 0 | 0 | 0 | 0 | 0 | 5 | 5 | 5 | 5 | 5 | 3 | 5 | 5 |
| 18 | 600 | 0 | 0 | 0 | 0 | 0 | 5 | 5 | 5 | 5 | 5 | 4 | 5 | 5 |
|   | 300 | 0 | 0 | 0 | 0 | 0 | 5 | 5 | 5 | 5 | 5 | 4 | 5 | 5 |
| 21 | 600 | 0 | 0 | 0 | 0 | 0 | 5 | 5 | 5 | 3 | 4 | 2 | 4 | 3 |
|   | 300 | 0 | 0 | 0 | 0 | 0 | 5 | 5 | 5 | 3 | 2 | 1 | 3 | 0 |
| 29 | 600 | 0 | 0 | 0 | 0 | 0 | 5 | 5 | 5 | 5 | 5 | 4 | 5 | 5 |
|   | 300 | 0 | 0 | 0 | 0 | 0 | 5 | 5 | 5 | 5 | 5 | 4 | 5 | 5 |
| 32 | 600 | 0 | 0 | 0 | 0 | 0 | 5 | 5 | 5 | 5 | 4 | 3 | 4 | 4 |
|   | 300 | 0 | 0 | 0 | 0 | 0 | 5 | 5 | 5 | 5 | 4 | 2 | 4 | 2 |
| 33 | 600 | 0 | 0 | 0 | 0 | 0 | 5 | 5 | 5 | 5 | 5 | 4 | 5 | 5 |
|   | 300 | 0 | 0 | 0 | 0 | 0 | 5 | 5 | 5 | 5 | 5 | 4 | 5 | 4 |
| 34 | 600 | 0 | 0 | 0 | 0 | 0 | 5 | 5 | 5 | 5 | 4 | 3 | 4 | 4 |
|   | 300 | 0 | 0 | 0 | 0 | 0 | 5 | 5 | 5 | 5 | 4 | 2 | 3 | 4 |
| 35 | 600 | 0 | 0 | 0 | 0 | 0 | 5 | 5 | 5 | 5 | 5 | 5 | 5 | 5 |
|   | 300 | 0 | 0 | 0 | 0 | 0 | 5 | 5 | 4 | 5 | 5 | 4 | 5 | 4 |
| 36 | 600 | 0 | 0 | 0 | 0 | 0 | 5 | 5 | 5 | 5 | 4 | 4 | 4 | 4 |
|   | 300 | 0 | 0 | 0 | 0 | 0 | 5 | 5 | 5 | 4 | 3 | 3 | 3 | 3 |
| 37 | 600 | 0 | 0 | 0 | 0 | 0 | 5 | 5 | 5 | 5 | 5 | 4 | 5 | 5 |
|   | 300 | 0 | 0 | 0 | 0 | 0 | 5 | 5 | 5 | 4 | 4 | 4 | 5 | 5 |
| 38 | 600 | 0 | 0 | 0 | 0 | 0 | 5 | 5 | 5 | 5 | 4 | 5 | 5 | 5 |
|   | 300 | 0 | 0 | 0 | 0 | 0 | 5 | 5 | 5 | 4 | 4 | 3 | 3 | 4 |
| 39 | 600 | 0 | 0 | 0 | 0 | 0 | 5 | 5 | 5 | 5 | 5 | 5 | 5 | 5 |
|   | 300 | 0 | 0 | 0 | 0 | 0 | 5 | 5 | 5 | 5 | 5 | 4 | 5 | 5 |
| 40 | 600 | 0 | 0 | 0 | 0 | 0 | 5 | 5 | 5 | 5 | 5 | 4 | 5 | 5 |

TABLE 3-continued

| Compound No. | Rate of application (g/10a) | a | b | c | d | e | f | g | h | i | j | k | l | m |
|---|---|---|---|---|---|---|---|---|---|---|---|---|---|---|
| 42 | 300 | 0 | 0 | 0 | 0 | 0 | 5 | 5 | 5 | 5 | 4 | 3 | 4 | 4 |
|  | 600 | 0 | 0 | 0 | 0 | 0 | 5 | 5 | 5 | 4 | 5 | 4 | 4 | 4 |
| 44 | 300 | 0 | 0 | 0 | 0 | 0 | 4 | 4 | 5 | 4 | 3 | 2 | 4 | 3 |
|  | 600 | 0 | 0 | 0 | 0 | 0 | 5 | 5 | 5 | 5 | 5 | 4 | 5 | 5 |
| 45 | 300 | 0 | 0 | 0 | 0 | 0 | 5 | 5 | 5 | 3 | 5 | 4 | 5 | 5 |
|  | 600 | 0 | 0 | 0 | 0 | 0 | 5 | 5 | 5 | 5 | 5 | 5 | 5 | 5 |
| 46 | 300 | 0 | 0 | 0 | 0 | 0 | 5 | 5 | 5 | 4 | 4 | 4 | 5 | 5 |
|  | 600 | 0 | 0 | 0 | 0 | 0 | 5 | 5 | 5 | 4 | 4 | 1 | 3 | 3 |
| 49 | 300 | 0 | 0 | 0 | 0 | 0 | 5 | 5 | 4 | 4 | 2 | 0 | 2 | 1 |
|  | 600 | 0 | 0 | 0 | 0 | 0 | 5 | 5 | 5 | 5 | 5 | 5 | 5 | 5 |
| 112 | 300 | 0 | 0 | 0 | 0 | 0 | 5 | 5 | 5 | 5 | 4 | 4 | 4 | 4 |
|  | 600 | 0 | 0 | 0 | 0 | 0 | 5 | 5 | 5 | 5 | 5 | 5 | 5 | 5 |
| 122 | 300 | 0 | 0 | 0 | 0 | 0 | 5 | 5 | 5 | 4 | 4 | 4 | 4 | 4 |
|  | 600 | 0 | 0 | 0 | 0 | 0 | 5 | 5 | 5 | 5 | 5 | 4 | 5 | 5 |
| 123 | 300 | 0 | 0 | 0 | 0 | 0 | 5 | 5 | 5 | 4 | 3 | 4 | 3 | 4 |
|  | 600 | 0 | 0 | 0 | 0 | 0 | 5 | 5 | 5 | 4 | 5 | 4 | 5 | 5 |
| 132 | 300 | 0 | 0 | 0 | 0 | 0 | 5 | 5 | 4 | 4 | 4 | 4 | 4 | 4 |
|  | 600 | 0 | 0 | 0 | 0 | 0 | 5 | 5 | 5 | 5 | 5 | 5 | 5 | 5 |
| 139 | 300 | 0 | 0 | 0 | 0 | 0 | 5 | 5 | 5 | 3 | 4 | 3 | 3 | 3 |
|  | 600 | 0 | 0 | 0 | 0 | 0 | 5 | 5 | 5 | 5 | 5 | 4 | 5 | 5 |
| 146 | 300 | 0 | 0 | 0 | 0 | 0 | 5 | 5 | 5 | 5 | 4 | 4 | 4 | 4 |
|  | 600 | 0 | 0 | 0 | 0 | 0 | 5 | 5 | 5 | 5 | 5 | 5 | 5 | 5 |
| 147 | 300 | 0 | 0 | 0 | 0 | 0 | 5 | 5 | 5 | 4 | 4 | 3 | 4 | 4 |
|  | 600 | 0 | 0 | 0 | 0 | 0 | 5 | 5 | 5 | 5 | 5 | 4 | 5 | 5 |
| 152 | 300 | 0 | 0 | 0 | 0 | 0 | 5 | 5 | 5 | 5 | 5 | 3 | 4 | 4 |
|  | 600 | 0 | 0 | 0 | 0 | 0 | 5 | 5 | 5 | 5 | 4 | 4 | 5 | 5 |
| 165 | 300 | 0 | 0 | 0 | 0 | 0 | 5 | 5 | 5 | 4 | 4 | 3 | 4 | 4 |
|  | 600 | 0 | 0 | 0 | 0 | 0 | 5 | 5 | 5 | 4 | 4 | 4 | 4 | 4 |
| 191 | 300 | 0 | 0 | 0 | 0 | 0 | 4 | 4 | 4 | 4 | 3 | 4 | 3 | 3 |
|  | 600 | 0 | 0 | 0 | 0 | 0 | 5 | 5 | 5 | 5 | 5 | 4 | 5 | 5 |
| 248 | 300 | 0 | 0 | 0 | 0 | 0 | 5 | 5 | 5 | 5 | 4 | 4 | 4 | 4 |
|  | 600 | 0 | 0 | 0 | 0 | 0 | 5 | 5 | 5 | 4 | 4 | 5 | 5 | 4 |
| 262 | 300 | 0 | 0 | 0 | 0 | 0 | 4 | 4 | 4 | 3 | 4 | 4 | 3 | 4 |
|  | 600 | 0 | 0 | 0 | 0 | 0 | 5 | 5 | 5 | 5 | 5 | 5 | 5 | 5 |
| 265 | 300 | 0 | 0 | 0 | 0 | 0 | 5 | 5 | 4 | 4 | 4 | 4 | 4 | 4 |
|  | 600 | 0 | 0 | 0 | 0 | 0 | 5 | 5 | 5 | 5 | 5 | 4 | 4 | 4 |
| A | 300 | 0 | 0 | 0 | 0 | 0 | 4 | 4 | 4 | 4 | 3 | 4 | 4 | 4 |
|  | 600 | 4 | 2 | 2 | 2 | 2 | 5 | 5 | 4 | 4 | 4 | 3 | 4 | 3 |
|  | 300 | 3 | 1 | 1 | 1 | 1 | 4 | 4 | 3 | 2 | 2 | 3 | 3 | 2 |

In Table 3, letters a to m in the column of "Plant" represent the following plants.
a: rice
b. wheat
c. corn
d. soybean
e. cotton
f. barnyard grass
g. large crabgrsss
h. green foxtail
i. pigweed
j. large smartweed
k. blue morning glory
l. yellow cyperus
m. hairy beggarticks

EXAMPLE 8

In the same way as in Example 7, each of the test compunds shown in Table 4 was subjected to a soil treatment test at lower rates of application, and the results are shown in Table 4.

A, B and C given in the column of Compouind No. in Table 4 represent the following compounds.
Compound A (same as in Example 7)

Compound B of the following formula

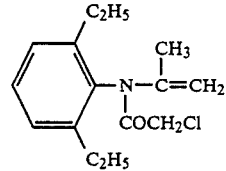

Compound C of the following formula

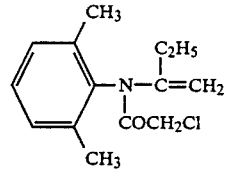

It is evident from the results given in Table 4 that the active compounds in accordance with this invention have better herbicidal activity than the comparative compounds A, B and C. The letters a to m given in the column of "Plant" in Table 4 have the same meanings as in Table 3.

TABLE 4

| Compound No. | Rate of application (g/10a) | a | b | c | d | e | f | g | h | i | j | k | l | m |
|---|---|---|---|---|---|---|---|---|---|---|---|---|---|---|
| 2 | 50 | 0 | 0 | 0 | 0 | 0 | 5 | 5 | 5 | 5 | 4 | 3 | 4 | 4 |
| 3 | 50 | 0 | 0 | 0 | 0 | 0 | 5 | 5 | 5 | 5 | 4 | 3 | 3 | 4 |
| 18 | 50 | 0 | 0 | 0 | 0 | 0 | 4 | 4 | 4 | 3 | 2 | 2 | 2 | 2 |
| 32 | 50 | 0 | 0 | 0 | 0 | 0 | 5 | 5 | 5 | 3 | 3 | 3 | 2 | 2 |
| 35 | 50 | 0 | 0 | 0 | 0 | 0 | 5 | 5 | 5 | 5 | 4 | 3 | 4 | 3 |
| 39 | 50 | 0 | 0 | 0 | 0 | 0 | 5 | 5 | 5 | 5 | 5 | 3 | 4 | 4 |
| 45 | 50 | 0 | 0 | 0 | 0 | 0 | 5 | 4 | 5 | 3 | 3 | 2 | 2 | 2 |
| 49 | 50 | 0 | 0 | 0 | 0 | 0 | 5 | 5 | 5 | 4 | 3 | 3 | 3 | 3 |
| 112 | 50 | 0 | 0 | 0 | 0 | 0 | 4 | 4 | 5 | 3 | 3 | 2 | 2 | 2 |
| 132 | 50 | 0 | 0 | 0 | 0 | 0 | 5 | 5 | 5 | 4 | 3 | 2 | 2 | 2 |
| 139 | 50 | 0 | 0 | 0 | 0 | 0 | 4 | 4 | 4 | 3 | 3 | 3 | 4 | 3 |
| 262 | 50 | 0 | 0 | 0 | 0 | 0 | 5 | 5 | 5 | 3 | 3 | 3 | 3 | 3 |
| A | 50 | 2 | 0 | 0 | 0 | 0 | 2 | 2 | 2 | 1 | 1 | 1 | 0 | 0 |
| B | 50 | 1 | 0 | 0 | 0 | 0 | 2 | 1 | 1 | 1 | 0 | 0 | 0 | 0 |
| C | 50 | 2 | 0 | 0 | 0 | 0 | 2 | 0 | 0 | 1 | 0 | 0 | 0 | 0 |

EXAMPLE 9

Upland farm soil (clay loam) was filled into porcelain pots (1/8850 ares), and seeds of various plants were sown in the soil to a depth of 0.5 to 1 cm, and grown in a greenhouse kept at an average atmospheric pressure of 25° C. Two weeks later, a water dilution of a wettable powder of each of the test compounds shown in Table 5, prepared as in Formulation Example 1, was sprayed onto the leaves of the plants at a predetermined rate of application. After the treatment, the plants were grown in a greenhouse, and two weeks later, the herbicidal effect of each of the test compounds was examined, and rated on the same standards as in Example 7. The results are shown in Table 5.

The letters representing the plants in Table 5 were the same as shown below Table 3.

TABLE 5

| Compound No. | Rate of application (g/10a) | a | b | c | f | g | h | d | e | i | j |
|---|---|---|---|---|---|---|---|---|---|---|---|
| 1 | 800 | 0 | 0 | 0 | 5 | 5 | 5 | 0 | 0 | 0 | 0 |
|   | 400 | 0 | 0 | 0 | 5 | 4 | 5 | 0 | 0 | 0 | 0 |
| 2 | 800 | 0 | 0 | 0 | 5 | 5 | 5 | 0 | 0 | 2 | 1 |
|   | 400 | 0 | 0 | 0 | 5 | 5 | 5 | 0 | 0 | 2 | 1 |
| 3 | 800 | 0 | 0 | 0 | 5 | 5 | 5 | 0 | 0 | 2 | 1 |
|   | 400 | 0 | 0 | 0 | 5 | 5 | 5 | 0 | 0 | 1 | 1 |
| 4 | 800 | 0 | 0 | 0 | 5 | 4 | 5 | 0 | 0 | 0 | 0 |
|   | 400 | 0 | 0 | 0 | 5 | 4 | 4 | 0 | 0 | 0 | 0 |
| 18 | 800 | 0 | 0 | 0 | 5 | 5 | 5 | 0 | 0 | 1 | 0 |
|   | 400 | 0 | 0 | 0 | 5 | 4 | 5 | 0 | 0 | 0 | 0 |
| 29 | 800 | 0 | 0 | 0 | 5 | 5 | 5 | 0 | 0 | 1 | 0 |
|   | 400 | 0 | 0 | 0 | 5 | 5 | 5 | 0 | 0 | 0 | 0 |
| 33 | 800 | 0 | 0 | 0 | 5 | 5 | 5 | 0 | 0 | 2 | 0 |
|   | 400 | 0 | 0 | 0 | 5 | 4 | 4 | 0 | 0 | 0 | 0 |
| 35 | 800 | 0 | 0 | 0 | 5 | 5 | 5 | 0 | 0 | 2 | 2 |
|   | 400 | 0 | 0 | 0 | 5 | 5 | 5 | 0 | 0 | 1 | 0 |
| 39 | 800 | 0 | 0 | 0 | 5 | 5 | 5 | 0 | 0 | 2 | 2 |
|   | 400 | 0 | 0 | 0 | 5 | 5 | 5 | 0 | 0 | 2 | 1 |
| 44 | 800 | 0 | 0 | 0 | 5 | 5 | 5 | 0 | 0 | 0 | 0 |
|   | 400 | 0 | 0 | 0 | 5 | 4 | 4 | 0 | 0 | 0 | 0 |
| 46 | 800 | 0 | 0 | 0 | 5 | 5 | 5 | 0 | 0 | 1 | 1 |
|   | 400 | 0 | 0 | 0 | 5 | 4 | 5 | 0 | 0 | 0 | 0 |

EXAMPLE 10

Paddy soil (alluvial soil) stirred after addition of water was filled into porcelain pots (1/8850 ares). Seeds of paddy weeds were sown and rice seedlings (variety: "akinishiki") in the 3-leaf stage were transplanted to a depth of 1 cm. Water was added to maintain a submerged state with a depth of 3 cm. A water dilution of a wettable powder of each of the test compounds shown in Table 6, prepared as in Formulation Example 1, was dropped at a predetermined rate of application onto the simulated paddy at the time of germination of the weeds. The plants were grown in a greenhouse kept at an average atmospheric temperature of 25° C. Three weeks later, the herbicidal effect of each of the test compounds was examined and rated on the same standard as in Example 7. The results are shown in Table 6. In the table, the letter f is the same as shown below Table 3, and the ltters n to q represent the following plants.

n: umbrella plant
o: three-squre grass
p: monochoria
q: broad-leaved weeds [false pimpernel, "azetogarashi" (*Vandellia angustifolia* Bentham) and "kikashigusa" (*Rotala Indica* Koehne.)]

TABLE 6

| Compound No. | Rate of application (g/10a) | Herbicidal effect | | | | | Transplanted rice |
|---|---|---|---|---|---|---|---|
| | | f | n | o | p | q | |
| 1 | 500 | 5 | 5 | 5 | 5 | 5 | 0 |
|   | 250 | 5 | 5 | 5 | 5 | 5 | 0 |
| 2 | 500 | 5 | 5 | 5 | 5 | 5 | 0 |
|   | 250 | 5 | 5 | 5 | 5 | 5 | 0 |
| 3 | 500 | 5 | 5 | 5 | 5 | 5 | 0 |
|   | 250 | 5 | 5 | 5 | 5 | 5 | 0 |
| 4 | 500 | 5 | 5 | 5 | 5 | 5 | 0 |
|   | 250 | 5 | 5 | 5 | 5 | 5 | 0 |
| 5 | 500 | 5 | 4 | 4 | 4 | 4 | 0 |
|   | 250 | 4 | 3 | 3 | 4 | 3 | 0 |
| 6 | 500 | 5 | 5 | 5 | 5 | 5 | 0 |
|   | 250 | 5 | 5 | 5 | 5 | 5 | 0 |
| 7 | 500 | 5 | 5 | 5 | 5 | 5 | 0 |
|   | 250 | 5 | 5 | 5 | 5 | 5 | 0 |
| 8 | 500 | 5 | 5 | 5 | 5 | 5 | 0 |
|   | 250 | 5 | 5 | 5 | 5 | 5 | 0 |
| 9 | 500 | 5 | 5 | 5 | 5 | 5 | 0 |
|   | 250 | 4 | 3 | 3 | 3 | 3 | 0 |
| 10 | 500 | 5 | 5 | 5 | 5 | 5 | 0 |
|   | 250 | 5 | 5 | 5 | 5 | 5 | 0 |
| 11 | 500 | 5 | 5 | 5 | 5 | 5 | 0 |
|   | 250 | 5 | 5 | 4 | 5 | 4 | 0 |
| 12 | 500 | 5 | 5 | 5 | 5 | 5 | 0 |
|   | 250 | 5 | 5 | 5 | 5 | 5 | 0 |
| 13 | 500 | 5 | 5 | 5 | 5 | 5 | 0 |
|   | 250 | 5 | 5 | 5 | 5 | 5 | 0 |
| 14 | 500 | 5 | 5 | 5 | 5 | 5 | 0 |
|   | 250 | 5 | 5 | 5 | 5 | 5 | 0 |
| 15 | 500 | 5 | 5 | 5 | 5 | 5 | 0 |
|   | 250 | 5 | 5 | 5 | 5 | 5 | 0 |

TABLE 6-continued

| Compound No. | Rate of application (g/10a) | Herbicidal effect | | | | | Transplanted rice |
|---|---|---|---|---|---|---|---|
| | | f | n | o | p | q | |
| 16 | 500 | 5 | 5 | 5 | 5 | 5 | 0 |
|    | 250 | 5 | 5 | 4 | 5 | 4 | 0 |
| 17 | 500 | 5 | 5 | 5 | 5 | 5 | 0 |
|    | 250 | 5 | 5 | 5 | 5 | 4 | 0 |
| 18 | 500 | 5 | 5 | 5 | 5 | 5 | 0 |
|    | 250 | 5 | 5 | 5 | 5 | 5 | 0 |
| 19 | 500 | 5 | 5 | 3 | 3 | 3 | 0 |
|    | 250 | 4 | 4 | 3 | 3 | 3 | 0 |
| 20 | 500 | 5 | 5 | 5 | 5 | 5 | 0 |
|    | 250 | 5 | 5 | 5 | 5 | 5 | 0 |
| 21 | 500 | 5 | 5 | 5 | 5 | 5 | 0 |
|    | 250 | 4 | 4 | 4 | 2 | 4 | 0 |
| 22 | 500 | 5 | 5 | 5 | 5 | 5 | 0 |
|    | 250 | 5 | 5 | 5 | 5 | 5 | 0 |
| 23 | 500 | 5 | 5 | 5 | 5 | 5 | 0 |
|    | 250 | 5 | 4 | 4 | 4 | 4 | 0 |
| 24 | 500 | 4 | 3 | 5 | 5 | 4 | 0 |
|    | 250 | 3 | 3 | 4 | 0 | 2 | 0 |
| 25 | 500 | 5 | 5 | 5 | 5 | 5 | 0 |
|    | 250 | 5 | 5 | 5 | 5 | 5 | 0 |
| 26 | 500 | 5 | 5 | 5 | 5 | 5 | 0 |
|    | 250 | 5 | 5 | 5 | 5 | 5 | 0 |
| 27 | 500 | 5 | 5 | 5 | 5 | 5 | 0 |
|    | 250 | 4 | 4 | 4 | 4 | 4 | 0 |
| 28 | 500 | 5 | 5 | 5 | 5 | 5 | 0 |
|    | 250 | 5 | 4 | 4 | 4 | 3 | 0 |
| 29 | 500 | 5 | 5 | 5 | 5 | 5 | 0 |
|    | 250 | 5 | 5 | 5 | 5 | 5 | 0 |
| 30 | 500 | 5 | 5 | 5 | 5 | 5 | 0 |
|    | 250 | 5 | 5 | 5 | 5 | 5 | 0 |
| 31 | 500 | 5 | 5 | 3 | 5 | 5 | 0 |
|    | 250 | 5 | 5 | 4 | 5 | 5 | 0 |
| 32 | 500 | 5 | 5 | 5 | 5 | 5 | 0 |
|    | 250 | 5 | 5 | 5 | 5 | 5 | 0 |
| 33 | 500 | 5 | 5 | 5 | 5 | 5 | 0 |
|    | 250 | 5 | 5 | 5 | 5 | 5 | 0 |
| 34 | 500 | 5 | 5 | 5 | 5 | 5 | 0 |
|    | 250 | 5 | 5 | 5 | 5 | 5 | 0 |
| 35 | 500 | 5 | 5 | 5 | 5 | 5 | 0 |
|    | 250 | 5 | 5 | 5 | 5 | 5 | 0 |
| 36 | 500 | 5 | 5 | 5 | 5 | 5 | 0 |
|    | 250 | 5 | 5 | 5 | 5 | 5 | 0 |
| 37 | 500 | 5 | 5 | 5 | 5 | 5 | 0 |
|    | 250 | 5 | 5 | 5 | 5 | 5 | 0 |
| 38 | 500 | 5 | 5 | 5 | 5 | 5 | 0 |
|    | 250 | 5 | 5 | 5 | 5 | 5 | 0 |
| 39 | 500 | 5 | 5 | 5 | 5 | 5 | 0 |
|    | 250 | 5 | 5 | 5 | 5 | 5 | 0 |
| 40 | 500 | 5 | 5 | 5 | 5 | 5 | 0 |
|    | 250 | 5 | 5 | 5 | 5 | 5 | 0 |
| 41 | 500 | 5 | 5 | 5 | 5 | 5 | 0 |
|    | 250 | 5 | 5 | 5 | 5 | 5 | 0 |
| 42 | 500 | 5 | 5 | 5 | 5 | 5 | 0 |
|    | 250 | 5 | 5 | 5 | 5 | 5 | 0 |
| 43 | 500 | 5 | 5 | 5 | 5 | 5 | 0 |
|    | 250 | 5 | 5 | 5 | 5 | 5 | 0 |
| 44 | 500 | 5 | 5 | 5 | 5 | 5 | 0 |
|    | 250 | 5 | 5 | 5 | 5 | 5 | 0 |
| 45 | 500 | 5 | 5 | 5 | 5 | 5 | 0 |
|    | 250 | 5 | 5 | 5 | 5 | 5 | 0 |
| 46 | 500 | 5 | 5 | 5 | 5 | 5 | 0 |
|    | 250 | 5 | 5 | 5 | 5 | 5 | 0 |
| 47 | 500 | 5 | 5 | 5 | 5 | 5 | 0 |
|    | 250 | 5 | 4 | 4 | 5 | 4 | 0 |
| 48 | 500 | 5 | 5 | 5 | 5 | 5 | 0 |
|    | 250 | 5 | 5 | 5 | 5 | 5 | 0 |
| 49 | 500 | 5 | 5 | 5 | 5 | 5 | 0 |
| 112 | 250 | 5 | 5 | 5 | 5 | 5 | 0 |
|     | 500 | 5 | 5 | 5 | 5 | 5 | 0 |
|     | 250 | 5 | 5 | 5 | 5 | 5 | 0 |
| 122 | 500 | 5 | 5 | 5 | 5 | 5 | 0 |
|     | 250 | 5 | 5 | 5 | 5 | 5 | 0 |
| 123 | 500 | 5 | 5 | 5 | 5 | 5 | 0 |
|     | 250 | 5 | 5 | 5 | 5 | 5 | 0 |
| 132 | 500 | 5 | 5 | 5 | 5 | 5 | 0 |
|     | 250 | 5 | 5 | 5 | 5 | 5 | 0 |
| 139 | 500 | 5 | 5 | 5 | 5 | 5 | 0 |
|     | 250 | 5 | 5 | 5 | 5 | 5 | 0 |
| 146 | 500 | 5 | 5 | 5 | 5 | 5 | 0 |
|     | 250 | 5 | 5 | 5 | 5 | 5 | 0 |
| 147 | 500 | 5 | 5 | 5 | 5 | 5 | 0 |
|     | 250 | 5 | 5 | 5 | 5 | 5 | 0 |
| 152 | 500 | 5 | 5 | 5 | 5 | 5 | 0 |
|     | 250 | 5 | 5 | 5 | 5 | 5 | 0 |
| 165 | 500 | 5 | 5 | 5 | 5 | 5 | 0 |
|     | 250 | 5 | 5 | 5 | 5 | 5 | 0 |
| 169 | 500 | 5 | 5 | 5 | 5 | 5 | 0 |
|     | 250 | 5 | 5 | 5 | 5 | 5 | 0 |
| 176 | 500 | 5 | 5 | 5 | 5 | 5 | 0 |
|     | 250 | 5 | 5 | 5 | 5 | 5 | 0 |
| 191 | 500 | 5 | 5 | 5 | 5 | 5 | 0 |
|     | 250 | 5 | 5 | 5 | 5 | 5 | 0 |
| 248 | 500 | 5 | 5 | 5 | 5 | 5 | 0 |
|     | 250 | 5 | 5 | 5 | 5 | 5 | 0 |
| 262 | 500 | 5 | 5 | 5 | 5 | 5 | 0 |
|     | 250 | 5 | 5 | 5 | 5 | 5 | 0 |
| 265 | 500 | 5 | 5 | 5 | 5 | 5 | 0 |
|     | 250 | 5 | 5 | 5 | 5 | 5 | 0 |

What is claimed is:

1. A haloacetamide compound of the formula (I)′

wherein
R₁ represents a substituted or unsubstituted phenyl group or a substituted or unsubstituted thienyl group, and
R represents a $C_1$–$C_6$ alkyl group; and
wherein the substituent of the substituted phenyl or thienyl group represented by $R_1$ is a member selected from the group consisting of $C_1$–$C_6$ alkyl groups, halogen atoms and $C_1$–$C_6$ alkoxy groups.

2. A herbicidal composition comprising a herbicidally effective amount of the haloacetamide compound of formula (I)′ set forth in claim 1, and an agriculturally acceptable diluent or carrier.

3. The herbicidal composition of claim 2 wherein the amount of the haloacetamide compound is about 0.1 to 90% by weight based on the weight of the composition.

4. A method of controlling the growth of undesired vegetation which comprises applying an effective amount of the haloacetamide compound of formula (I)′ set forth in claim 1 to the locus to be protected from the undesired vegetation.

5. The method of claim 4 wherein the amount of the haloacetamide compound of formula (I)′ is about 2 to about 3,000 g/10 ares.

* * * * *